(12) United States Patent
Stassinopoulos et al.

(10) Patent No.: US 10,688,166 B2
(45) Date of Patent: Jun. 23, 2020

(54) COMPOSITIONS AND METHODS FOR IMPROVED CAR-T CELL THERAPIES

(71) Applicant: CERUS CORPORATION, Concord, CA (US)

(72) Inventors: Adonis Stassinopoulos, Dublin, CA (US); William Mariner Greenman, Lafayette, CA (US)

(73) Assignee: CERUS CORPORATION, Concord, CA (US)

( * ) Notice: Subject to any disclaimer, the term of this patent is extended or adjusted under 35 U.S.C. 154(b) by 0 days.

(21) Appl. No.: 15/524,233

(22) PCT Filed: Nov. 2, 2015

(86) PCT No.: PCT/US2015/058678
§ 371 (c)(1),
(2) Date: May 3, 2017

(87) PCT Pub. No.: WO2016/073381
PCT Pub. Date: May 12, 2016

(65) Prior Publication Data
US 2017/0354724 A1 Dec. 14, 2017

Related U.S. Application Data

(60) Provisional application No. 62/074,489, filed on Nov. 3, 2014.

(51) Int. Cl.
| | | |
|---|---|---|
| *A61K 39/00* | (2006.01) | |
| *A61K 35/17* | (2015.01) | |
| *C12N 5/0783* | (2010.01) | |
| *A61P 35/00* | (2006.01) | |
| *A61K 9/00* | (2006.01) | |
| *C07K 14/725* | (2006.01) | |
| *C07K 14/705* | (2006.01) | |
| *C07K 16/28* | (2006.01) | |
| *A61K 38/00* | (2006.01) | |

(52) U.S. Cl.
CPC ........ *A61K 39/0011* (2013.01); *A61K 9/0019* (2013.01); *A61K 35/17* (2013.01); *A61P 35/00* (2018.01); *C07K 14/7051* (2013.01); *C07K 14/70578* (2013.01); *C07K 16/2803* (2013.01); *C12N 5/0636* (2013.01); *A61K 38/00* (2013.01); *A61K 2039/505* (2013.01); *A61K 2039/5156* (2013.01); *C07K 2317/622* (2013.01); *C07K 2319/02* (2013.01); *C07K 2319/03* (2013.01); *C07K 2319/33* (2013.01); *C07K 2319/40* (2013.01); *C07K 2319/74* (2013.01); *C12N 2510/02* (2013.01)

(58) Field of Classification Search
CPC .......................... A61K 35/00; A61K 39/0011
See application file for complete search history.

(56) References Cited

U.S. PATENT DOCUMENTS

| | | |
|---|---|---|
| 5,359,046 A | 10/1994 | Capon et al. |
| 5,399,719 A | 3/1995 | Wollowitz et al. |
| 5,571,698 A | 11/1996 | Ladner et al. |
| 5,593,823 A | 1/1997 | Wollowitz et al. |
| 5,686,281 A | 11/1997 | Roberts |
| 5,888,530 A | 3/1999 | Netti et al. |
| 6,057,098 A | 5/2000 | Buechler et al. |
| 6,090,611 A | 7/2000 | Covacci et al. |
| 6,093,725 A | 7/2000 | Cook |
| 6,103,521 A | 8/2000 | Capon et al. |
| 6,514,987 B1 | 2/2003 | Cook et al. |
| 7,695,725 B2* | 4/2010 | Dubensky, Jr. ........ A61K 39/07 424/235.1 |
| 8,383,099 B2 | 2/2013 | Dudley et al. |
| 2002/0150588 A1 | 10/2002 | Allison et al. |
| 2003/0224520 A1* | 12/2003 | June .................. C12N 5/0634 435/455 |
| 2004/0197343 A1 | 10/2004 | Dubensky et al. |
| 2004/0228877 A1 | 11/2004 | Dubensky et al. |
| 2005/0281783 A1 | 12/2005 | Kinch et al. |
| 2007/0009497 A1 | 1/2007 | Steinman et al. |
| 2015/0320799 A1* | 11/2015 | Low ................ A61K 47/48061 424/93.21 |

FOREIGN PATENT DOCUMENTS

| | | | | |
|---|---|---|---|---|
| WO | 9639820 A1 | 12/1996 | | |
| WO | 9903976 A2 | 1/1999 | | |
| WO | WO2014/100615 | * 12/2003 | ......... | A61K 31/4985 |
| WO | 2005009463 | 2/2005 | | |
| WO | WO2005/009463 | * 2/2005 | ............ | A61K 39/02 |

(Continued)

OTHER PUBLICATIONS

Xu et al. Cancer Let 2014;172-8.*
Wei et al. Exp Hematol Oncol 2017;6:10, pp. 1-7.*
Zhang et al. J Hematol Oncol 2017;10:1, pp. 1-11.*
Xu et al. (Cancer Letters. Feb. 28, 2014. 343(2):172-178). (Year: 2014).*
International Search Report and Written Opinion dated Jan. 29, 2016 in PCT/US2015/058678 (11 pages).
Gargett et al., "The inducible caspase-9 suicide gene system as a "safety switch" to limit on-target, off-tumor toxicities of chimeric antigen receptor T cells", Front Pharmacol. Oct. 28, 2014;5:235. doi: 10.3389/fphar.2014.00235.eCollection 2014.

(Continued)

*Primary Examiner* — Scott Long
(74) *Attorney, Agent, or Firm* — Acuity Law Group, PC; Michael A. Whittaker

(57) ABSTRACT

The present invention relates to the preparation and use in recipients of CAR-T cell-derived effector cells which are modified to limit their proliferation within the recipient. This is accomplished through the introduction of adducts into the nucleic acids of CAR-T cell-derived effector cells following expansion in vitro to provide expanded and activated CAR-T cell-derived effector cells that retain immunologic function, including the expression of one ore more cytokines.

39 Claims, 2 Drawing Sheets

(56) References Cited

FOREIGN PATENT DOCUMENTS

| WO | 2012068360 A1 | 5/2012 |
|---|---|---|
| WO | 2014100615 | 6/2014 |

OTHER PUBLICATIONS

Fitzgerald et al., "Cytokine Release Syndrome After Chimeric Antigen Receptor T Cell Therapy for Acute Lymphoblastic Leukemia", Online Clinical Investigations, Feb. 2017, vol. 45, No. 2, pp. e124-e131.
Hossain et al., "Amotosalen-Treated Donor T Cells Have Polyclonal Antigen-Specific Long-Term Function without Graft-versus-Host Disease after Allogeneic Bone Marrow Transplantation", Biology of Blood and Marrow Transplantation, 11:169-180 (2005).
Roback et al., "Allogeneic T Cells Treated with Amotosalen Prevent Lethal Cytomegalovirus Disease without Producing Graft-versus-Host Disease Following Bone Marrow Transplantation", J Immunol., 2003; 171:6023-6031.
Rodgers et al., "Switch-mediated activation and retargeting of CAR-T cells for B-cell malignancies", PNAS, Jan. 2016, E459-E468.
Yakes and Van Houten, Mitochondrial DNA damage is more extensive and persists longer than nuclear DNA damage in human cells following oxidative stress. Proc Natl Acad Sci U S A. Jan. 21, 1997;94(2):514-519.
Yarmush et al., Coupling of antibody-binding fragments to solid-phase supports: site-directed binding of F(ab')2 fragments. J Biochem Biophys Methods. Dec. 1992;25(4):285-297.
Zaremba et al., Identification of an Enhancer Agonist Cytotoxic T Lymphocyte Peptide from Human Carcinoembryonic Antigen. Cancer Res. Oct. 15, 1997;57(20):4570-4577.
Zimmerman et al., Expression of annexin II in conventional renal cell carcinoma is correlated with Fuhrman grade and clinical outcome. Virchows Arch. Oct. 2004;445(4):368-374.
The Extnded European Search Report issued in EP 15856769 dated Jun. 15, 2018.
Grass et al., Allogenic cell therapy of graft versus host disease with psoralen photochemically-treated (PCT) donor leukocytes . Cytokine,1997;9(11):894 abstract #18.
Abutaily et al., Cadherins, catenins and APC in pleural malignant mesothelioma. J Pathol. Nov. 2003;201(3):355-362.
Altwein and Luboldt, Prognostic Factors for Carcinoma of the Prostate. Urol Int. 1999;63(1):62-71.
Andersen and thor Straten, Survivin—a universal tumor antigen. Histol Histopathol. Apr. 2002;17(2):669-675.
Argani et al., Discovery of New Markers of Cancer through Serial Analysis of Gene Expression Prostate Stem Cell Antigen Is Overexpressed in Pancreatic Adenocarcinoma. Cancer Res. Jun. 1, 2001;61(11):4320-4324.
Arora et al., Identification of Differentially Expressed Genes in Oral Squamous Cell Carcinoma. Mol Carcinog. Feb. 2005;42(2):97-108.
Arslan et al., A new approach to sequence comparison: normalized sequence alignment. Bioinformatics. Apr. 2001;17(4):327-337.
Auerbuch et al., Development of a Competitive Index Assay to Evaluate the Virulence of Listeria monocytogenes actAMutants during Primary and Secondary Infection of Mice. Infect Immun. Sep. 2001;69(9):5953-5957.
Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Bondurant et al., Definition of an Immunogenic RegionWithin the OvarianTumor Antigen Stratum Comeum Chymotryptic Enzyme. Clin Cancer Res. May 1, 2005;11(9):3446-3454.
Brezniceanu et al., HMGB1 inhibits cell death in yeast and mammalian cells and is abundantly expressed in human breast carcinoma. FASEB J. Jul. 2003;17(10):1295-1297.
Brinkmann et al., Novel Genes in the PAGE and GAGE Family of Tumor Antigens Found by Homology Walking in be dbEST Database. Cancer Res. Apr. 1, 1999;59(7):1445-1448.

Brockstedt et al., Killed but metabolically active microbes: a new vaccine paradigm for eliciting effector T-cell responses and protective immunity. Nat Med. Aug. 2005;11(8):853-860.
Bronte et al., Genetic Vaccination with "Self" Tyrosinase-related Protein 2 Causes Melanoma Eradication but not Vitiligo. Cancer Res. Jan. 15, 2000;60(2):253-258.
Capurro et al., Glypican-3: A Novel Serum and Histochemical Marker for Hepatocellular Carcinoma. Gastroenterology. Jul. 2003;125(1):89-97.
Carpenito et al., Control of large, established tumor xenografts with genetically retargeted human T cells containing CD28 and CD137 domains. Proc Natl Acad Sci U S A. Mar. 3, 2009;106(9):3360-3365.
Chan et al., In Situ Hybridization Study of PSP94 (Prostatic Secretory Protein of 94 Amino Acids) Expression in Human Prostates. Prostate. Oct. 1, 1999;41(2):99-109.
Chang et al., A Phase I Trial of Tumor Lysate-Pulsed Dendritic Cells in the Treatment of Advanced Cancer. Clin Cancer Res. Apr. 2002;8(4):1021-1032.
Chen et al., Immunodominant CD4+ responses identified in a patient vaccinated with full-length NY-ESO-1 formulated with ISCOMATRIX adjuvant. Proc Natl Acad Sci U S A. Jun. 22, 2004;101(25):9363-9368.
Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.
Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.
Clements et al., Adenomatous Polyposis Coli/β-Catenin Interaction and Downstream Targets: Altered Gene Expression in Gastrointestinal Tumors. Clin Colorectal Cancer Aug. 2003;3(2):113-120.
Clifton et al., A chlamydial type III translocated protein is tyrosine-phosphorylated at the site of entry and associated with recruitment of actin. Proc Natl Acad Sci USA. Jul. 6, 2004;101(27):10166-10171.
Clinton et al., A Comparative Study of Four Serological Tumor Markers for the Detection of Breast Cancer. Biomed Sci Instrum. 2003;39:408-414.
Cobaleda et al., A primitive hematopoietic cell is the target for the leukemic transformation in human Philadelphia-positive acute lymphoblastic leukemia. Blood. Feb. 1, 2000;95(3):1007-1013.
Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.
Creighton et al., Mechanisms and catalysts of disulfide bond formation in proteins. Trends Biotechnol. Jan. 1995;13(1):18-23.
Cwirla et al., Peptides on phage: a vast library of peptides for identifying ligands. Proc Natl Acad Sci U S A. Aug. 1990;87(16):6378-6382.
Dalerba et al., MAGE, BAGE and GAGE gene expression in human rhabdomyosarcomas. Int J Cancer. Jul. 1, 2001;93(1):85-90.
Davies et al., Characterisation of a recombinant Fv fragment of anti-MUC1 antibody HMFG1. Cancer Lett. Jul. 29, 1994;82(2):179-184.
De Backer et al., Characterization of the GAGE Genes That Are Expressed in Various Human Cancers and in Normal Testis. Cancer Res. Jul. 1, 1999;59(13):3157-3165.
Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.
Devlin et al., Random peptide libraries: a source of specific protein binding molecules Science. Jul. 27, 1990;249(4967):404-406.
Disis and Cheever, HER-2/Neu Protein: A Target for Antigen-Specific Immunotherapy of Human Cancer. Adv Cancer Res. 1997;71:343-371.
Disis et al., Humoral Epitope-Spreading Following Immunization with a HER-2/neu Peptide Based Vaccine in Cancer Patients. J Clin Immunol. Sep. 2004;24(5):571-578.

(56) References Cited

OTHER PUBLICATIONS

Dobrzanski et al., Tc1 and Tc2 Effector Cell Therapy Elicit Long-Term Tumor Immunity by Contrasting Mechanisms That Result in Complementary Endogenous Type 1 Antitumor Responses. J Immunol. Feb. 1, 2004;172(3):1380-1390.
Dosaka-Akita et al., Expression of N-Acetylglucosaminyltransferase V Is Associated with Prognosis and Histology in Non-Small Cell Lung Cancers. Clin Cancer Res. Mar. 1, 2004;10(5)1773-1779.
Dropulic and June, Gene-based immunotherapy for human immunodeficiency virus infection and acquired immunodeficiency syndrome. Hum Gene Ther. Jun. 2006;17(6):577-588.
Dull et al., A Third-Generation Lentivirus Vector with a Conditional Packaging System. J Virol. Nov. 1998;72(11):8463-8471.
Duxbury et al., CEACAM6 as a novel target for indirect type 1 immunotoxin-based therapy in pancreatic adenocarcinoma. Biochem Biophys Res Commun. May 7, 2004;317(3):837-843.
Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.
Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.
Fang et al., Expression of Dnmt1, demethylase, MeCP2 and methylation of tumor-related genes in human gastric cancer. World J Gastroenterol. Dec. 1, 2004;10(23):3394-3398.
Faure et al., Inducible Hsp70 as Target of Anticancer Immunotherapy: Identification of HLA-A*0201-Restricted Epitopes. Int J Cancer. Mar. 1, 2004;108(6):863-870.
Fleishhauer et al., The DAM Gene Family Encodes a New Group of Tumor-specific Antigens Recognized by Human Leukocyte Antigen Al-restricted Cytotoxic T Lymphocytes. Cancer Res. Jul. 15, 1998;58(14):2969-2972.
Fong et al., Altered peptide ligand vaccination with Flt3 ligand expanded dendritic cells for tumor immunotherapy. Proc Natl Acad Sci U S A. Jul. 17, 2001;98(15):8809-8814.
Fuessel et al., Multiple tumor marker analyses (PSA, hK2, PSCA, trp-p8) in primary prostate cancers using quantitative RT-PCR. Int J Oncol. Jul. 2003;23(1):221-228.
Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60 (1):146-148.
Garcia-Hernandez et al., Adoptive Transfer of Tumor-Specific Tc17 Effector T Cells Controls the Growth of B16 Melanoma in Mice. J Immunol. Apr. 15, 2010;184(8):4215-4227.
Ghazizadeh et al., Role of cdk4, p16INK4, and Rb Expression in the Prognosis of Bronchioloalveolar Carcinomas. Respiration. Jan.-Feb. 2005;72(1):68-73.
Gilliam et al., A phase II study of G17DT in gastric carcinoma. Eur J Surg Oncol. Jun. 2004;30(5):536-543.
Grimm et al., Mouse alpha-fetoprotein-specific DNA-based immunotherapy of hepatocellular carcinoma leads to tumor regression in mice. Gastroenterology. Oct. 2000;119(4):1104-1112.
Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.
Guegen et al., An Antigen Recognized by Autologous CTLs on a Human Bladder Carcinoma. J Immunol. Jun. 15, 1998;160(12):6188-6194.
Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.
Hakansson et al., Establishment and phenotypic characterization of human U937 cells with inducible P210 BCR/ABL expression reveals upregulation of CEACAM1 (CD66a). Leukemia. Mar. 2004;18(3):538-547.

Harris et al., The Biological and Therapeutic Importance of Gastrin Gene Expression in Pancreatic Adenocarcinomas. Cancer Res. Aug. 15, 2004;64(16):5624-5631.
Hassan et al., Mesothelin: A New Target for Immunotherapy. Clin Cancer Res. Jun. 15, 2004;10(12 Pt 1):3937-3942.
Hei et al., Elimination of cytokine production in stored platelet concentrate aliquots by photochemical treatment with psoralen plus ultraviolet A light. Transfusion. Mar. 1999;39(3):239-248.
Hirose et al., Incidence of Diffuse Large B-Cell Lymphoma of Germinal Center B-Cell Origin in Whole Diffuse Large B-Cell Lymphoma: Tissue Fluorescence in Situ Hybridization Using t(14;18) Compared with Immunohistochemistry. Int J Hematol. Jan. 2005,81(1):48-57.
Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003,63(24):8614-8622.
Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.
Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2):242-250.
Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.
Kann and Goldstein, Performance Evaluation of a New Algorithm for the Detection of Remote Homologs With Sequence Comparison. Proteins. Aug. 1, 2002;48(2):367-376.
Kubuschok et al., Expression of cancer testis antigens in pancreatic carcinoma cell lines, pancreatic adenocarcinoma and chronic pancreatitis. Int J Cancer Apr. 20, 2004;109(4):568-575.
Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.
Laheru and Jaffee, Immunotherapy for pancreatic cancer—science driving clinical progress. Nat Rev Cancer. Jun. 2005;5(6):459-467.
Lee et al., Current concepts in the diagnosis and management of cytokine release syndrome. Blood. Jul. 10, 2014;124(2):188-195.
Lee et al., Immunomic analysis of human sarcoma Proc Natl Acad Sci U S A. Mar. 4, 2003;100(5):2651-2656.
Lee et al., T cells expressing CD19 chimeric antigen receptors for acute lymphoblastic leukaemia in children and young adults: a phase 1 dose-escalation trial. Lancet. Feb. 7, 2015;385(9967):517-528—with Supp Data (20 pages total).
Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.
Li et al., Expression Profile of Cancer-Testis Genes in 121 Human Colorectal Cancer Tissue and Adjacent Normal Tissue. Clin Cancer Res. Mar. 1, 2005;11(5):1809-1814.
Liang et al., Microvessel density, cyclo-oxygenase 2 expression, K-ras mutation and p53 overexpression in colonic cancer Br J Surg. Mar. 2004;91(3):355-361.
Lim et al., Molecular and phenotypic spectrum of de novo Philadelphia positive acute leukemia. Int J Mol Med. Dec. 1999;4(6):665-667.
Lin et al., Melanoma-Associated Antigens in Esophageal Adenocarcinoma Identification of Novel MAGE-A10 Splice Variants. Clin Cancer Res. Sep. 1, 2004;10(17):5708-5716.
Lucas et al., MAGE-B5, MAGE-B6, MAGE-C2, and MAGE-C3: four new members of the MAGE family with tumor-specific expression. Int J Cancer Jul. 1, 2000;87(1):55-60.
Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Mandruzzato et al., A CASP-8 Mutation Recognized by Cytolytic T Lymphocytes on a Human Head and Neck Carcinoma. J Exp Med. Aug. 29, 1997;186(5):785-793.

(56) References Cited

OTHER PUBLICATIONS

Matsumoto et al., Expression of the SART-1 antigens in uterine cancers. Jpn J Cancer Res. Dec. 1998;89 (12):1292-1295.
Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.
Maus et al., Antibody-modified T cells: CARs take the front seat for hematologic malignancies. Blood. Apr. 24, 2014;123(17):2625-2635.
Mayo et al., Mdm-2 Phosphorylation by DNA-dependent Protein Kinase Prevents Interaction with p53. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Moreau-Aubry et al., A Processed Pseudogene Codes for a New Antigen Recognized by a Cd8+ T Cell Clone on Melanoma. J Exp Med. May 1, 2000;191(9):1617-1624.
Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. Jun. 1999;5(6):1331-1338.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer Nov. 17, 2003;89(10):1934-1939.
Muminova et al., Characterization of human mesothelin transcripts in ovarian and pancreatic cancer. BMC Cancer. May 12, 2004;4:19.
Munsen and Rodbard, Ligand: A Versatile Computerized Approach for Characterization of Ligand-Binding Systems. Anal Biochem. Sep. 1, 1980;107(1):220-239.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Cellular and humoral immune responses to a human pancreatic cancer antigen, coactosin-like protein, originally defined by the SEREX method. Eur J Immunol. Mar. 2002;32(3):826-836.
Vakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.
Naldini et al., In Vivo Gene Delivery and Stable Transduction of Nondividing Cells by a Lentiviral Vector Science. Apr. 12, 1996;272(5259)263-267.
Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.
Nicoletto et al., BRCA-1 and BRCA-2 mutations as prognostic factors in clinical practice and genetic counselling. Cancer Treat Rev. Oct. 2001;27(5):295-304.
Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.
Otte et al., MAGE-A Gene Expression Pattern in Primary Breast Cancer Cancer. Res. Sep. 15, 2001;61(18):6682-6687.
Pisarev et al., Full-length dominant-negative survivin for cancer immunotherapy. Clin Cancer Res. Dec. 15, 2003;9(17):6523-6533.
Porter et al., Chimeric Antigen Receptor—Modified T Cells in Chronic Lymphoid Leukemia. N Engl J Med. Aug. 25, 2011;365(8):725-733.
Renkvist et al., A listing of human tumor antigens recognized by T cells. Cancer Immunol Immunother. Mar. 2001;50(1):3-15.
Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.
Rosenberg et al, Use of Tumor-Infiltrating Lymphocytes and Interleukin-2 in the Immunotherapy of Patients with Metastatic Melanoma. A preliminary report. N Engl J Med. Dec. 22, 1998;319(25):1676-1680.
Rozinov and Nolan, Evolution of peptides that modulate the spectral qualities of bound, small-molecule fluorophores. Chem Biol. Dec. 1998;5(12):713-728.
Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma cells. Cancer Res. Oct. 1, 1997;57(19):4348-4355.
Santin et al., The serine protease stratum corneum chymotryptic enzyme (kallikrein 7) is highly overexpressed in squamous cervical cancer cells. Gynecol Oncol. Aug. 2004;94(2):283-288.
Sarcevic et al., Expression of Cancer/Testis Tumor Associated Antigens in Cervical Squamous Cell Carcinoma. Oncology. 2003;64(4):443-449.
Sarobe et al., Carcinoembryonic Antigen as a Target to Induce Anti-Tumor Immune Responses. Curr Cancer Drug Targets. Aug. 2004;4(5):443-454.
Sasaki et al., SAGE mRNA expression in advanced-stage lung cancers. Eur J Surg Oncol. Dec. 2003;29(10):900-903.
Sasatomi et al., Expression of tumor rejection antigens in colorectal carcinomas. Cancer. Mar. 15, 2002;94(6):1636-1641.
Scanlan et al., Antigens recognized by autologous antibody in patients with renal-cell carcinoma. Int J Cancer. Nov. 12, 1999;83(4):456-464.
Scanlan et al., Cancer-related serological recognition of human colon cancer: identification of potential diagnostic and immunotherapeutic targets. Cancer Res. Jul. 15, 2002;62(14):4041-4047.
Scanlan et al., Expression of cancer-testis antigens in lung cancer: definition of bromodomain testis-specific gene (BRDT) as a new CT gene, CT9. Cancer Lett. Mar. 31, 2000;150(2):155-164.
Scanlan et al., Humoral immunity to human breast cancer: antigen definition and quantitative analysis of mRNA expression. Cancer Immun. Mar. 30, 2001;1:4.
Scanlan et al., The cancer/testis genes: review, standardization, and commentary. Cancer Immun. Jan. 23, 2004;4:1.
Scarcella et al., Expression of MAGE and GAGE in high-grade brain tumors: a potential target for specific Immunotherapy and diagnostic markers. Clin Cancer Res. Feb. 1999;5(2):335-341.
Schmittgen et al., Expression of prostate specific membrane antigen and three alternatively spliced variants of PSMA in prostate cancer patients. Int J Cancer. Nov. 1, 2003;107(2):323-329.
Schwartz et al., Novel targeted and immunotherapeutic strategies in chronic myeloid leukemia. Semin Hematol. Jan. 2003;40(1):87-96.
Scott and Smith, Searching for peptide ligands with an epitope library. Science. Jul. 27, 1990;249(4967):386-390.
Sepehr et al., Distinct pattern of TP53 mutations in squamous cell carcinoma of the esophagus in Iran. Oncogene. Nov. 1, 2001;20(50):7368-7374.
Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.
Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.

(56) References Cited

OTHER PUBLICATIONS

Shirasawa et al., Receptor for advanced glycation end-products is a marker of type I lung alveolar cells. Genes Cells. Feb. 2004;9(2):165-174.
Siegel et al., Induction of antitumour immunity using survivin peptide-pulsed dendritic cells in a murine lymphoma model. Br J Haematol. Sep. 2003;122(6):911-914.
Slager et al., Identification of multiple HLA-DR-restricted epitopes of the tumor-associated antigen CAMEL by CD4+ Th1/Th2 lymphocytes. J Immunol. Apr. 15, 2004;172(8):5095-5102.
Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 1, 2004;(3)227-236.
Small et al., Immunotherapy of Hormone-Refractory Prostate Cancer With Antigen-Loaded Dendritic Cells. J Clin Oncol. Dec. 1, 2000;18(23):3894-3903.
Stams et al., Expression Levels of TEL, AML1, and the Fusion ProductsTEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8)2974-2980.
Steffens et al., Immunohistochemical analysis of tumor antigen saturation following injection of monoclonal antibody G250. Anticancer Res. Mar.-Apr. 1999;19(2A):1197-1200.
Stolier et al., Initial experience with surgical treatment planning in the newly diagnosed breast cancer patient at high risk for BRCA-1 or BRCA-2 mutation. Breast J. Nov.-Dec. 2004;10(6):475-480.
Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.
Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8)1363-1370.
Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.
Tanaka et al., Expression of Tumor-Rejection Antigens in Gynecologic Cancers. Jpn J Cancer Res. Nov. 2000;91(11)1177-1184.
Tannapfel et al., BRAF Gene Mutations Are Rare Events in Gastroenteropancreatic Neuroendocrine Tumors. Am J Clin Pathol. Feb. 2005;123(2):256-2601.
Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.
TSAO and SOBER, Melanoma Treatment Update. Dermatol Clin. Apr. 2005;23(2):323-333.
Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).
Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.
Virok et al., Chlamydial Infection Induces Pathobiotype-Specific Protein Tyrosine Phosphorylation in Epithelial Cells. Infect Immun. Apr. 2005;73(4):1939-1946.
Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.
Naltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.
Wang et al., Alterations of APC, c-met, and p53 Genes in Tumor Tissue and Serum of Patients with Gastric Cancers. J Surg Res. Aug. 2004;120(2):242-248.
Wang et al., Cloning Genes Encoding MHC Class II—Restricted Antigens: Mutated CDC27 as a Tumor Antigen. Science. May 21, 1999;284(5418):1351-1354.
Wang et al., Identification of a Novel Major Histocompatibility Complex Class II—restricted Tumor Antigen Resulting from a Chromosomal Rearrangement Recognized by CD4+ T Cells. J Exp Med. May 17, 1999;189(10):1659-1668.
Ward et al., Binding activities of a repertoire of single immunoglobulin variable domains secreted from *Escherichia coli*. Nature. Oct. 12, 1989;341(6242):544-546.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Woycechowsky and Raines, Native Disulfide Bond Formation in Proteins. Curr Opin Chem Biol. Oct. 2000;4(5):533-539.
Park et al., "CD19-targeted CAR T-cell therapeutics for hematologic malignancies: interpreting clinical outcomes to date", Blood, Jun. 30, 2016 x vol. 127, No. 26, pp. 3312-3320.
Brockstedt et al., "Listeria-based cancer vaccines that segregate immunogenicity from toxicity", PNAS, Sep. 21, 2004, vol. 101, No. 38, 13832-13837.
Louis et al., "Antitumor activity and long-term fate of chimeric antigen receptor—positive T cells in patients with neuroblastoma", Blood. Dec. 1, 2011; 118(23): 6050-6056.
Brockstedt et al., "Killed but metabolically active microbes: a new vaccine paradigm for eliciting effector T-cell responses and protective immunity", Nature Medicine, vol. 11, No. 8, Aug. 2005, 853-860.
Harty and Badovinac, "Shaping and reshaping CD8+ T-cell memory", Nature Reviews, Immunology, vol. 8, Feb. 2008, pp. 107-119.
Skoberne et al., "KBMA Listeria monocytogenes is an effective vector for DC-mediated induction of antitumor immunity", The Journal of Clinical Investigation, http://www.jci.org, vol. 118, No. 12, Dec. 2008, pp. 3990-4001.

\* cited by examiner

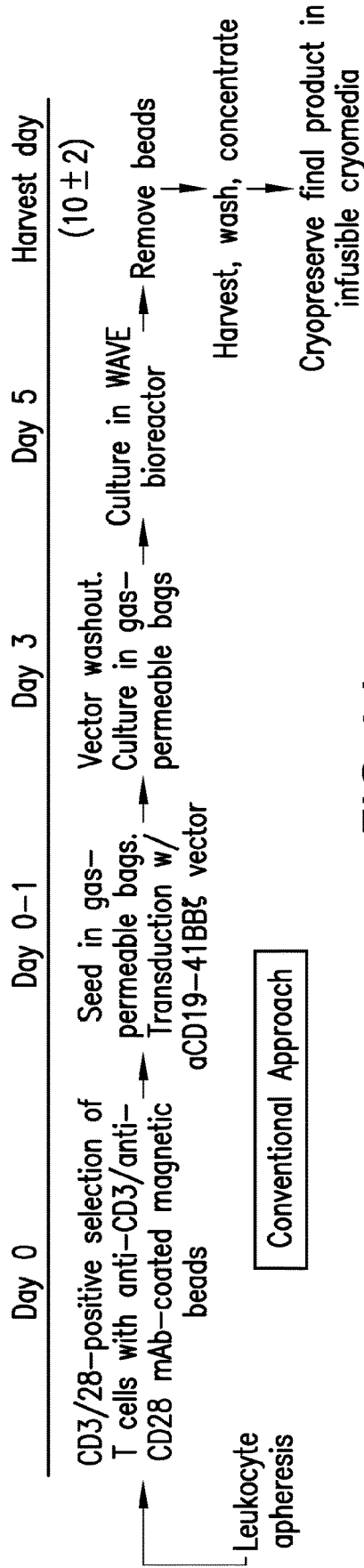
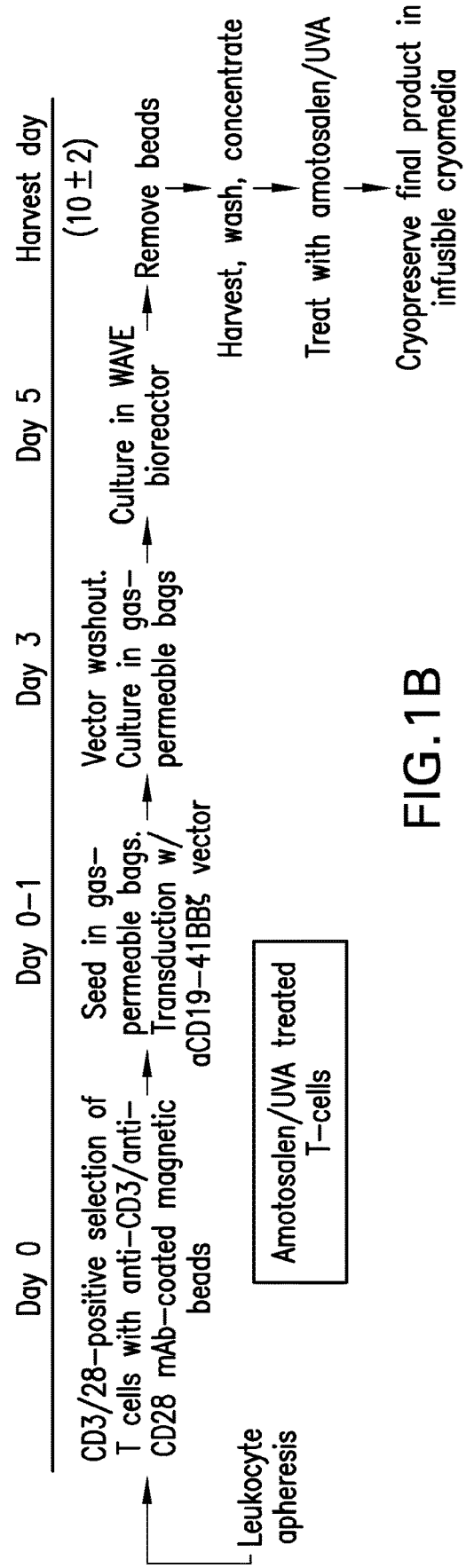

COMPOSITIONS AND METHODS FOR IMPROVED CAR-T CELL THERAPIES

The present invention is filed under 35 U.S.C. § 371 as the U.S. national phase of International Patent Application No. PCT/US2015/058678, filed Nov. 2, 2015, which designated the United States and claims priority from U.S. Provisional Patent Application 62/074,489 filed Nov. 3, 2014, each of which is hereby incorporated in its entirety including all tables, figures, and claims.

BACKGROUND OF THE INVENTION

The following discussion of the background of the invention is merely provided to aid the reader in understanding the invention and is not admitted to describe or constitute prior art to the present invention.

Autologous adoptive cell transfer involves the collection, modification and return of a patient's immune cells, offering a promising immunotherapeutic approach for the treatment of different types of cancers. Typically, leukocytes are isolated, usually by well-established density barrier centrifugation, and T lymphocytes are expanded ex vivo using cell culture methods, often relying on the immunomodulatory action of interleukin-2. Once expanded, the cells are administered intravenously to the patent in an activated state. Such cells are referred to as effector T cells. In addition, a combination of anti-CD3 and anti-CD28 antibodies are commonly used as a surrogate for antigen presentation with appropriate co-stimmulation cues to promote the proliferation of T cells in culture. Research into interleukin-21 suggests it may also play an important role in enhancing the efficacy of T cell based therapies prepared in this manner. Other interleukins can also be used in these cultures, with an overall objective of enhancing the cytolytic function of the exampanded T lymphocytes, once re-infused into the autologous subject.

For T cells, engagement of the CD4$^+$ and CD8$^+$ T cell receptor (TCR) alone is not sufficient to induce persistent activation of resting naive or memory T cells. Fully functional, productive T cell activation requires a second co-stimulatory signal from a competent antigen-presenting cell (APC). Co-stimulation is achieved naturally by the interaction of the co-stimulatory cell surface receptor on T cells, known as CD28, with the appropriate counter-receptors on the surface of the APC, known as CD80 and CD86. An APC is normally a cell of host origin which displays a moiety which will cause the stimulation of an immune response. APCs include monocyte/macrophages, dendritic cells (DCs), B cells, and any number of virally-infected or tumor cells which express a protein on their surface recognized by T cells, and can also be used for the antigen-dependent activation of T cells. To induce functional activation rather than toleragenic T cells, APCs must also express on their surface a co-stimulatory molecule. Such APCs are capable of stimulating T cell proliferation, inducing cytokine production, and acting as targets for cytolytic T lymphocytes (CTL) upon direct interaction with the T cell. Several receptors that have been reported to provide co-stimulation for T-cell activation, including CD28, OX40, CD27, CD2, CD5, ICAM-1, LFA-1 (CD11a/CD18), and 4-1BB. The signaling pathways utilized by these co-stimulatory molecules share the common property of acting in synergy with the primary T cell receptor activation signal. These costimmulatory cues for T cell activation are alternatively referred to as Signal 2 and/or Signal 3; Signal 1 is presentation by APCs of epitopes on MHC class I or MHC class II restriction elements.

Recently, T cells have been genetically engineered to produce artificial T cell receptors on their surface called chimeric antigen receptors, or CARs. CARs are proteins that allow T cells to recognize a specific, pre-selected protein, or antigen, found on targeted tumor cells. CAR-T cells can be cultured and expanded in the laboratory, then re-infused to patients in a similar manner to that described above for adoptive transfer of native T cells. Through the guidance of the engineered T cell receptor, CAR-T cells recognize and destroy the cancer cells that display the specific antigen on their surfaces. In 2014, the first chimeric antigen receptor T (CAR-T) cell-based immunotherapy, known as CTL019, received breakthrough drug designation from the US Food and Drug Administration for the treatment of relapsed and refractive acute lymphoblastic leukemia (ALL).

Cytokine-associated toxicity, also referred to as a "cytokine storm" or more recently as cytokine release syndrome (CRS), is a common and potentially lethal complication of CAR-T cell therapy. CRS is a non-antigen specific toxicity that can occur as a result of the high-levels of CAR-T cell expansion and immune activation typically required to mediate clinical benefit using modern immunotherapies such as CAR-T cell transfer. Timing of symptom onset and CRS severity depends on the inducing agent and the magnitude of immune cell activation. Symptom onset typically occurs days to occasionally weeks after T cell infusion, coinciding with maximal in vivo T-cell expansion. In recent reports of CRS following adoptive T-cell therapy for cancer, the incidence and severity of the syndrome is greater when patients have large tumor burdens, due to the expression of production of proinflammatory cytokines such as TNF-α by the adoptively transferred expanding and activated CAR-T cell populations. CRS associated with adoptive T-cell therapies has been consistently associated with elevated IFNγ, IL-6, and TNFa levels, and increases in IL-2, granulocyte macrophage-colony-stimulating factor (GM-CSF), IL-10, IL-8, IL-5, and fracktalkine have also been reported.

There remains a need in the art to provide improved methods and compositions for CAR-T cell therapies, particularly for the safety of these novel medical interventions.

BRIEF SUMMARY OF THE INVENTION

The present invention relates to the preparation and use in recipients of CAR-T cell-derived effector cells which are modified to limit their proliferation within the recipient. This is accomplished through the introduction of adducts into the genomic nucleic acids of CAR-T cell-derived effector cells following expansion in vitro which prevent further division of the expanded and activated CAR-T cell-derived effector cells. Because some degree of cytokine release is likely a necessary consequence of T cell activation and therefore efficacy, of CAR-T cell-based therapy, the adducts are introduced with a frequency necessary to prevent cell division (and so further T cell proliferation), but that permits the CAR-T cell-derived effector cells to retain immunologic function (e.g., complete immunologic function, partial immunologic function), including the expression of one or more effector cytokines.

In a first aspect, the present invention relates to a CAR-T cell-derived effector cell population that is attenuated for proliferation. The cell population comprises a population of activated T cells expressing a chimeric antigen receptor (CAR), the CAR comprising an extracellular domain which specifically binds a predetermined targeted antigen. The nucleic acids of the activated T cells have been modified by reaction with a nucleic acid targeting compound that reacts directly with the nucleic acid (e.g., modified by reaction with a nucleic acid targeting compound). In certain embodiments, the activated T cells are attenuated for proliferation) due to the introduction in crosslinks within the cell's nucleic acid. Preferably, these crosslinks incluse inter-strand crosslinks in the cell's genomic DNA.

In various embodiments, the activated T cells are present in the population in a therapeutically effective amount for treatment of a malignancy that expresses the predetermined antigen. Thus, in preferred embodiments, the activated T cells are provided in a pharmaceutically acceptable excipient which supports maintenance of the activated T cells. Suitable buffers and salts are well known in the art for maintenance and administration of T cells for adoptive cell transfer.

The term "attenuated for proliferation" as used herein refers to proliferation being inhibited in at least 50% of the CAR-T-derived effector cells. In certain embodiments, the nucleic acid targeting agent is present in an amount effective to form from about $10^2$ to about $10^4$ adducts per $10^8$ base pairs of genomic DNA of the leukocytes. Preferably, the method results in proliferation being inhibited in at least 75%, 90%, and most preferably at least 95%, at least 99%, at least 99.9%, or at least 99.99% or more of the CAR-T-derived effector cells. Suitable nucleic acid targeting agents comprise an alkylator selected from the group consisting of mustards, mustard intermediates and mustard equivalents; a nucleic acid targeting group selected from the group consisting of intercalators, minor groove binders, major groove binders, electrostatic binders, and sequence-specific binders; β-alanine; N-(acridin-9-yl), 2-[bis(2-chloroethyl)amino] ethyl ester; or a photoactivatable moiety selected from the group consisting of furocoumarins, actinomycins, anthracyclinones, anthramycins, benzodipyrones, fluorenes, fluorenones, monostral fats blue, norphillin A, organic dyes; phenanthridines, phenazathionium salts, phenazines, phenothiazines, phenylazides, quinolines and thiaxanthenones acridines and ellipticenes. Preferred ones are psoralen compounds activated by UVA irradiation. In a preferred embodiment, the psoralen is 4'-(4-amino-2-oxa)butyl-4,5',8-trimethylpsoralen, 4'aminomethyl 4, 5', 8-trimethylpsoralen (AMT), 5-methoxy psoralen, trioxalen 4, 5' 8-trimethylpsoralen, or 8-methoxy psoralen. This list is not meant to be limiting.

Most preferably, the nucleic acid targeting compound is activated by irradiation, which may be a psoralen compound activated by UVA irradiation. The CAR-T cell-derived effector cell population can comprise psoralen-induced interstrand crosslinks introduced between the strands of the genomic DNA double helix (e.g., interstrand crosslinks that inhibit replication of the activated T cells as described hereinafter).

Because cytokine release is a necessary consequence of T cell activation and efficacy, for effective CAR-T cell-based therapy, it is preferred that at least a portion of the activated T cells produce one or more cytokines, such as one or more cytokines selected from the group consisting of IL-1β IL-2, TNF-α, and IFN-γ. Additionally, at least a portion of the activated T cells preferably express one or more surface markers selected from the group consisting of CD2, CD28, CTLA4, CD40 ligand (gp39), CD18, CD25, CD69, CD16/CD56, MHC Class I, MHC Class II, CD8, CD4, CD3/TcR, CD54, LFA-1 and VLA-4.

When an antitumor chimeric antigen receptor is utilized, the tumor may be of any kind as long as it has a cell surface antigen which may be recognized by the chimeric receptor. In certain embodiments, a CAR-T cell-derived effector cell population targets a cancer selected from the group consisting of lung cancer, melanoma, breast cancer, pancreatic cancer, gastric cancer, hepatocellular carcinoma, prostate cancer, colon cancer, renal cell carcinoma, ovarian cancer, neuroblastoma, rhabdomyosarcoma, leukemia and lymphoma. In various embodiments then, predetermined antigen is a cancer antigen, and preferably is selected from the antigens listed in Table 1.

In a related aspect, the present invention relates to a method of inducing a T-cell response to at least one predetermined antigen in a subject, comprising administering to the subject a CAR-T cell-derived effector cell population as described herein in an amount sufficient to induce an antitumor response to a cancer in the subject, wherein the cancer expresses the predetermined antigen.

In another related aspect, the present invention relates to methods for preparing a CAR-T cell-derived effector cell population comprising a population of activated T cells expressing a chimeric antigen receptor (CAR), the CAR comprising an extracellular domain which specifically binds a predetermined antigen, and where the CAR-T cell-derived effector cell population is attenuated for proliferation. These methods comprise:

contacting in vitro one or more T cells that have been modified to express the CAR with a stimulus that induces expansion of the T cells to provide an expanded T cell population;

modifying the nucleic acid of the T cells in the expanded T cell population by reaction with a nucleic acid targeting compound that reacts directly with the nucleic acid so that the T cells in the expanded T cell population are attenuated for proliferation; and prior to or following the modifying step, activating in vitro the T cells to produce an effector T cell population. In accordance with these methods, the T cells in the resulting effector T cell population are preferably attenuated for proliferation.

As described herein, the CAR-T cells of the present invention are expanded and activated in vitro to provide a sufficient CAR-T cell-derived effector cell population that is attenuated for further proliferation in vivo in the subject receiving the CAR-T cell therapy. The expansion step necessarily precedes modification of the nucleic acid which renders the cells attenuated for proliferation. The activation step, however, may precede or follow modification of the nucleic acid. Thus, in certain embodiments, the method comprises contacting the one or more T cells with the predetermined antigen under conditions in which the T cells are both induced to expand and are activated by the same stimulus, and the T cells in the expanded T cell population are attenuated for proliferation following expansion and activation. In alternative embodiments, the stimulus that induces expansion of the T cells can be a non-specific expansion stimulus, and the expanded T cell population may be subsequently activated by contacting the T cells in the expanded T cell population with the predetermined antigen under conditions in which the T cells are activated. In these latter embodiments, the T cells in the expanded T cell population may be attenuated for proliferation either before or following the activation step.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE FIGURES

FIG. 1A depicts an exemplary manufacturing procedure for CAR-T cells.

FIG. 1B depicts an exemplary manufacturing procedure for the CAR-T-derived effector cells of the present invention.

DETAILED DESCRIPTION OF THE INVENTION

Figure 2:
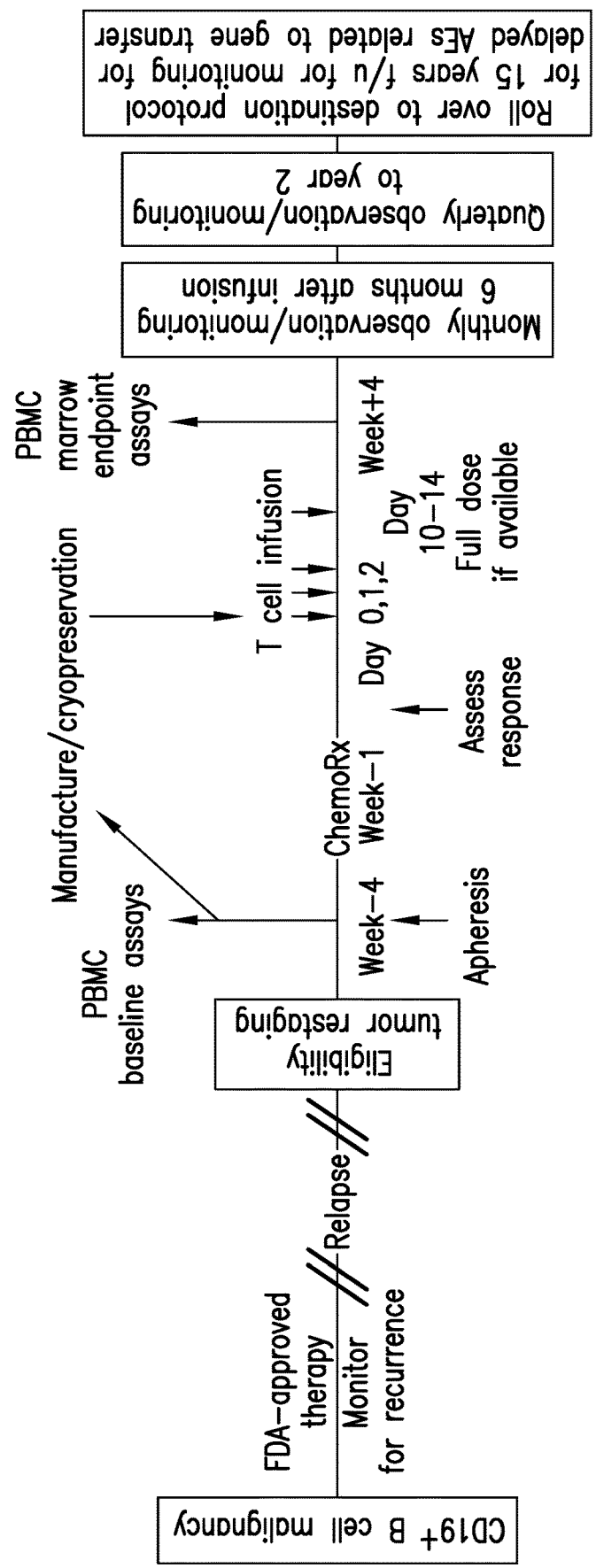
FIG. 2 depicts an exemplary therapy protocol for administration of the CAR-T-derived effector cells of the present invention, using CD19+ B cell malignancy as a model system.

The present invention relates to the preparation and use of CAR-T cells which exhibit a reduced propensity for initiating cytokine release syndrome due to uncontrolled expansion in vivo resulting from recognition of the antigen present on targeted tumors, following administration to a subject. As noted above, CRS severity can depend on the magnitude of immune cell activation and proliferation, which is correlated to the extent of the tumor or tumor cell burden expressing the targeted antigen. By inducing activation and proliferation ex vivo and treating the cells so as to inhibit further proliferation in vivo following administration, the CAR-T-derived effector cells of the present invention retain the ability to specifically target disease, but with reduced complications.

"CAR-T cells" refer to a T cell or population thereof, which has been modified through molecular biological methods to express a chimeric antigen receptor (CAR) on the T cell surface. The CAR is a polypeptide having a pre-defined binding specificity to a desired target expressed operably connected to (e.g., as a fusion, separate chains linked by one or more disulfide bonds, etc.) the intracellular part of a T-cell activation domain. By bypassing MHC class I and class II restriction, CAR engineered T cells of both $CD8^+$ and $CD4^+$ subsets can be recruited for redirected target cell recognition. The most common CARs are fusions of immuoglobulin binding functionality (e.g., as a single-chain variable fragment (scFv) derived from a monoclonal antibody) to CD3-zeta (CD3ζ) transmembrane and endodomain. Such molecules result in the transmission of a zeta signal in response to recognition by the immuoglobulin binding functionality of its target. There are, however, many alternatives. By way of example, an antigen recognition domain from native T-cell receptor (TCR) alpha and beta single chains may be used as the binding functionality. Alternatively, receptor ectodomains (e.g. CD4 ectodomain) or cytokines (which leads to recognition of cells bearing the cognate cytokine receptor) may be employed. All that is required of the binding functionality is that it binds a given target with high affinity in a specific manner.

"Specifically" or "selectively" binds, when referring to a ligand/receptor, nucleic acid/complementary nucleic acid, antibody/antigen, or other binding pair (e.g., a cytokine to a cytokine receptor) indicates a binding reaction which is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound.

In a typical embodiment a molecule that specifically binds a target will have an affinity that is at least about $10^6$ liters/mol ($K_D=10^{-6}M$), and preferably at least about $10^8$ liters/mol, as determined, e.g., by Scatchard analysis (Munsen, et al. (1980) Analyt. Biochem. 107:220-239). It is recognized by the skilled artisan that some binding compounds can specifically bind to more than one target, e.g., an antibody specifically binds to its antigen, to lectins by way of the antibody's oligosaccharide, and/or to an Fc receptor by way of the antibody's Fc region.

Activation of a CAR-T cell refers to a process by which the cells recognize and respond to binding of the chimeric end of their antigen-specific receptors to the corresponding antigen. The most immediate consequence of TCR activation is the initiation of signaling pathways including induction of specific protein tyrosine kinases (PTKs), breakdown of phosphatidylinositol 4,5-biphosphate (PIP2), activation of protein kinase C (PKC) and elevation of intracellular calcium ion concentration. These early events are transmitted to the nucleus and result in clonal expansion of the cells, upregulation of activation markers (e.g., CD25, CD71, CD26, CD27, CD28, CD30, CD154 CD40L, and CD134) on the cell surface, differentiation into effector cells, induction of cytotoxicity or cytokine secretion, and/or induction of apoptosis. Surface marker expression and cell proliferation are typically assessed by flow cytometry. Activated CAR-T cells are referred to herein as "CAR-T-derived effector cells."

To prevent CAR-T cells from undergoing activation-induced cell death and anergy, CD28 costimulation may be employed. CD28 is the prototype of a family of costimulatory molecules that is physiologically engaged on T cells by binding to the respective ligands on antigen-presenting cells (APCs). The agonistic CD28 ligands B7.1 (CD80) and B7.2 (CD86), physiologically expressed on APCs, are missing on most cancer cells with the consequence that the CD3ζ CAR upon binding to cancer cells does not provide the costimulation required for full activation. The limitation may be overcome by linking the intracellular signaling domain of CD28 to CD3ζ in one polypeptide chain of the same CAR. The artificial fusion of the CD28 and CD3ζ signaling domains facilitates Lck-mediated CD28 phosphorylation that binds and activates phosphatidylinositol 3-kinase for downstream signaling, resulting in full T-cell activation and IL-2 release. Other costimulatory molecules of the TNF-receptor family including 4-1BB (CD137) and OX40 (CD134) can also be integrated into the same CD3ζ CAR molecule or combined with CD28 in a CAR. This type of CAR has the advantage that T-cell costimulation occurs in an APC-independent fashion and is accompanied by suppressing inhibitory and/or strengthening stimulatory signals, each costimulatory signal modulating the T-cell effector function in a specific but undesirable fashion. CD28 costimulation is integrated into most currently used CARs because CD28 sustains survival and prolongs polyclonal expansion of engineered T cells without the need of B7-CD28 engagement.

One drawback to the use of CAR-T cells in subjects has been the initiation of CRS in some recipients. Severe cases are known as cytokine storms, and are similar to the cytokine storm seen in severe sepsis. In most patients, CRS symptoms are usually mild and flulike, with fevers and myalgias. However, some patients experience a severe inflammatory syndrome, including vascular leak, hypotension, pulmonary edema, and coagulopathy, resulting in multiorgan system failure. In patients with severe CRS associated with T cell-engaging therapies, IL-6 levels reportedly peak during maximal T cell proliferation.

Thus, the present invention limits CRS by controlling levels of CAR-T cell-derived effector cells in the recipient. This is accomplished through the introduction of adducts into the CAR-T cell-derived effector cells following expansion in vitro which inhibit (e.g., prevent) further division of the expanded and activated CAR-T cell-derived effector cells. Because some degree of cytokine release is likely a necessary consequence of T cell activation and therefore efficacy, of CAR-T cell-based therapy, the adducts are introduced in an amount necessary to prevent cell division (and so T cell proliferation), but that permits the CAR-T cell-derived effector cells to retain immunologic function, including the expression of effector cytokines.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

1. Definitions

"Administration" as it applies to a human, primate, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

As used herein, an "analog" or "derivative" with reference to a peptide, polypeptide or protein refers to another peptide, polypeptide or protein that possesses a similar or identical function as the original peptide, polypeptide or protein, but does not necessarily comprise a similar or identical amino acid sequence or structure of the original peptide, polypeptide or protein. An analog preferably satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the original amino acid sequence (b) a proteinaceous agent encoded by a nucleotide sequence that hybridizes under stringent conditions to a nucleotide sequence encoding the original amino acid sequence; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the original amino acid sequence.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells. Dendritic cells occur in at least two lineages. The first lineage encompasses pre-DC1, myeloid DC1, and mature DC1. The second lineage encompasses $CD34^+$ $CD45RA^-$ early progenitor multipotent cells, $CD34^+$ $CD45RA^+$ cells, $CD34^+CD45RA^+CD4^+IL-3R\alpha^+$ pro-DC2 cells, $CD4^+CD11c^-$ plasmacytoid pre-DC2 cells, lymphoid human DC2 plasmacytoid-derived DC2s, and mature DC2s.

"Attenuation" and "attenuated" encompasses a bacterium, virus, parasite, infectious organism, prion, cell (e.g., tumor cell, T cell), gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the $LD_{50}$, the rate of clearance from an organ, or the competitive index (see, e.g., Auerbuch, et al. (2001) Infect. Immunity 69:5953-5957). Generally, an attenuation results an increase in the $LD_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

"Attenuated gene" encompasses a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition.

An "extracellular fluid" encompasses, e.g., serum, plasma, blood, interstitial fluid, cerebrospinal fluid, secreted fluids, lymph, bile, sweat, fecal matter, and urine. An "extracelluar fluid" can comprise a colloid or a suspension, e.g., whole blood or coagulated blood.

The term "fragments" in the context of polypeptides include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a larger polypeptide.

"Gene" refers to a nucleic acid sequence encoding an oligopeptide or polypeptide. The oligopeptide or polypeptide can be biologically active, antigenically active, biologically inactive, or antigenically inactive, and the like. The term gene encompasses, e.g., the sum of the open reading frames (ORFs) encoding a specific oligopeptide or polypeptide; the sum of the ORFs plus the nucleic acids encoding introns; the sum of the ORFs and the operably linked promoter(s); the sum of the ORFS and the operably linked promoter(s) and any introns; the sum of the ORFS and the operably linked promoter(s), intron(s), and promoter(s), and other regulatory elements, such as enhancer(s). In certain embodiments, "gene" encompasses any sequences required in cis for regulating expression of the gene. The term gene can also refer to a nucleic acid that encodes a peptide encompassing an antigen or an antigenically active fragment of a peptide, oligopeptide, polypeptide, or protein. The term gene does not necessarily imply that the encoded peptide or protein has any biological activity, or even that the peptide or protein is antigenically active. A nucleic acid sequence encoding a non-expressable sequence is generally considered a pseudogene. The term gene also encompasses nucleic acid sequences encoding a ribonucleic acid such as rRNA, tRNA, or a ribozyme.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

"Ligand" refers to a small molecule, peptide, polypeptide, or membrane associated or membrane-bound molecule, that is an agonist or antagonist of a receptor. "Ligand" also encompasses a binding agent that is not an agonist or antagonist, and has no agonist or antagonist properties. By convention, where a ligand is membrane-bound on a first cell, the receptor usually occurs on a second cell. The second cell may have the same identity (the same name), or it may have a different identity (a different name), as the first cell. A ligand or receptor may be entirely intracellular, that is, it may reside in the cytosol, nucleus, or in some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Nucleic acid" refers to deoxyribonucleotides or ribonucleotides and polymers thereof in either single stranded, double-stranded form, or multi-stranded form. Non-limiting examples of a nucleic acid are a, e.g., cDNA, mRNA, oligonucleotide, and polynucleotide. A particular nucleic acid sequence can also implicitly encompasses "allelic variants" and "splice variants."

"Operably linked" in the context of a promoter and a nucleic acid encoding a mRNA means that the promoter can be used to initiate transcription of that nucleic acid.

The terms "percent sequence identity" and "% sequence identity" refer to the percentage of sequence similarity found by a comparison or alignment of two or more amino acid or nucleic acid sequences. Percent identity can be determined by a direct comparison of the sequence information between two molecules by aligning the sequences, counting the exact number of matches between the two aligned sequences, dividing by the length of the shorter sequence, and multiplying the result by 100. An algorithm for calculating percent identity is the Smith-Waterman homology search algorithm (see, e.g., Kann and Goldstein (2002) Proteins 48:367-376; Arslan, et al. (2001) Bioinformatics 17:327-337).

By "purified" and "isolated" is meant, when referring to a polypeptide, that the polypeptide is present in the substantial absence of the other biological macromolecules with which it is associated in nature. The term "purified" as used herein means that an identified polypeptide often accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the polypeptides present. The weights of water, buffers, salts, detergents, reductants, protease inhibitors, stabilizers (including an added protein such as albumin), and excipients, and molecules having a molecular weight of less than 1000, are generally not used in the determination of polypeptide purity. See, e.g., discussion of purity in U.S. Pat. No. 6,090,611 issued to Covacci, et al.

"Peptide" refers to a short sequence of amino acids, where the amino acids are connected to each other by peptide bonds. A peptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A "peptide" may be connected to another moiety by way of a peptide bond or some other type of linkage. A peptide is at least two amino acids in length and generally less than about 25 amino acids in length, where the maximal length is a function of custom or context. The terms "peptide" and "oligopeptide" may be used interchangeably.

"Protein" generally refers to the sequence of amino acids comprising a polypeptide chain. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

"Recombinant" when used with reference, e.g., to a nucleic acid, cell, animal, virus, plasmid, vector, or the like, indicates modification by the introduction of an exogenous, non-native nucleic acid, alteration of a native nucleic acid, or by derivation in whole or in part from a recombinant nucleic acid, cell, virus, plasmid, or vector. Recombinant protein refers to a protein derived, e.g., from a recombinant nucleic acid, virus, plasmid, vector, or the like. "Recombinant bacterium" encompasses a bacterium where the genome is engineered by recombinant methods, e.g., by way of a mutation, deletion, insertion, and/or a rearrangement. "Recombinant bacterium" also encompasses a bacterium modified to include a recombinant extra-genomic nucleic acid, e.g., a plasmid or a second chromosome, or a bacterium where an existing extra-genomic nucleic acid is altered.

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

A "selectable marker" encompasses a nucleic acid that allows one to select for or against a cell that contains the selectable marker. Examples of selectable markers include, without limitation, e.g.: (1) A nucleic acid encoding a product providing resistance to an otherwise toxic compound (e.g., an antibiotic), or encoding susceptibility to an otherwise harmless compound (e.g., sucrose); (2) A nucleic acid encoding a product that is otherwise lacking in the recipient cell (e.g., tRNA genes, auxotrophic markers); (3) A nucleic acid encoding a product that suppresses an activity of a gene product; (4) A nucleic acid that encodes a product that can be readily identified (e.g., phenotypic markers such as beta-galactosidase, green fluorescent protein (GFP), cell surface proteins, an epitope tag, a FLAG tag); (5) A nucleic acid that can be identified by hybridization techniques, for example, PCR or molecular beacons.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology.

"Therapeutically effective amount" is defined as an amount of a reagent or pharmaceutical composition that is sufficient to induce a desired immune response specific for encoded heterologous antigens, show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.).

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival.

2. CAR-T Cells

The term "chimeric receptor" as used herein is defined as a cell-surface receptor comprising an extracellular ligand binding domain, a transmembrane domain and a cytoplasmic co-stimulatory signaling domain in a combination that is not naturally found together on a single protein. This particularly includes receptors wherein the extracellular domain and the cytoplasmic domain are not naturally found together on a single receptor protein. Further, the chimeric receptor is different from the TCR expressed in the native T cell lymphocyte.

As described in U.S. Pat. Nos. 5,359,046, 5,686,281 and 6,103,521, the extracellular domain may be obtained from any of the wide variety of extracellular domains or secreted proteins associated with ligand binding and/or signal transduction. The extracellular domain may be part of a protein which is monomeric, homodimeric, heterodimeric, or associated with a larger number of proteins in a non-covalent complex. In particular, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

As described herein, the extracellular domains of CARs are often derived from immunoglobulins. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present. The antibodies so identified may then be further analyzed for affinity and specificity in the CAR design selected.

When an antitumor chimeric receptor is utilized, the tumor may be of any kind as long as it has a cell surface antigen which may be recognized by the chimeric receptor. In a specific embodiment, the chimeric receptor may be for any cancer for which a specific monoclonal antibody exists or is capable of being generated. In particular, cancers such as neuroblastoma, small cell lung cancer, melanoma, ovarian cancer, renal cell carcinoma, colon cancer, Hodgkin's lymphoma, and acute lymphoblastic leukemia (e.g., childhood acute lymphoblastic leukemia) have antigens which may be targeted by the chimeric receptors. The compositions and methods of this invention can be used in immunotherapy in the treatment of cancer, in particular the treatment of lung cancer, melanoma, breast cancer, prostate cancer, colon cancer, renal cell carcinoma, ovarian cancer, neuroblastoma, rhabdomyosarcoma, leukemia and lymphoma. The compositions and methods described in the present invention may be utilized in conjunction with other types of therapy for cancer, such as chemotherapy, surgery, radiation, gene therapy, and so forth, as described hereinafter.

The transmembrane domain may be contributed by the protein contributing the multispecific extracellular inducer clustering domain, the protein contributing the effector function signaling domain, the protein contributing the proliferation signaling portion, or by a totally different protein. For the most part it will be convenient to have the transmembrane domain naturally associated with one of the domains. In some cases it will be desirable to employ the transmembrane domain of the ζ, η or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. In some instances, the transmembrane domain will be selected or modified by amino acid substitution to avoid binding of such domains to the transmembrane domains of the same or different surface membrane proteins to minimize interactions with other members of the receptor complex. In other cases it will be desirable to employ the transmembrane domain of ζ, η or FcεR1γ chains and -β, MB1 (Igα), B29 or CD3γ, ζ, or ε, in order to retain physical association with other members of the receptor complex. Examples of suitable transmembrane regions for use with the invention include the constant (Fc) regions of immunoglobins, human CD8a, and artificial linkers that serve to move the targeting moiety away from the cell surface for improved access to and binding on target cells, however any transmembrane region sufficient to anchor the CAR in the membrane can be used. Persons of skill are aware of numerous transmembrane regions and the structural elements (such as lipophilic amino acid regions) that produce transmembrane domains in numerous membrane proteins and therefore can substitute any convenient sequence.

The cytoplasmic domain of the chimeric receptors of the invention can comprise a signaling domain (e.g., co-stimulatory signaling domain) by itself or combined with any other desired cytoplasmic domain(s) useful in the context of this chimeric receptor type, such as for example, a 4-1BB signaling domain, a CD3ζ signaling domain and/or a CD28 signaling domain. The 4-1BB, CD3ζ and CD28 signaling domains are well characterized, including for example, their use in chimeric receptors. In one embodiment, the cytoplasmic domain of the chimeric receptors can comprise the 4-1BB signaling domain by itself or combined with any other desired cytoplasmic domain(s) useful in the context of this chimeric receptor type. In a most preferred embodiment of the invention the extracellular domain comprises a single chain variable domain of a monoclonal antibody, the transmembrane domain comprises the hinge and transmembrane domain of CD8α, and the cytoplasmic domain comprises the signaling domain of CD3ζ and the signaling domain of 4-1BB. The CD8α hinge and transmembrane domain consists of 69 amino acids translated from the 207 nucleotides at positions 815-1021 of GenBank Accession No. NM_001768. The CD3ζ signaling domain of the preferred embodiment contains 112 amino acids translated from 339 nucleotides at positions 1022-1360 of GenBank Accession No. NM_000734.

In adoptive immunotherapy, the patient's circulating lymphocytes, or tumor infiltrated lymphocytes, are isolated in vitro, activated by lymphokines such as IL-2 or transduced with genes for tumor necrosis, and readministered. To achieve this, one would administer to an animal, or human patient, an immunologically effective amount of activated lymphocytes genetically modified to express a tumor-specific chimeric receptor gene as described herein. The activated lymphocytes will most preferably be the patient's own cells that were earlier isolated from a blood or tumor sample and activated and expanded in vitro. The antigen-specific CAR-T cells can be expanded in vitro for use in adoptive cellular immunotherapy in which infusions of such cells have been shown to have anti-tumor reactivity in a tumor-bearing host.

Genetic modification for introduction of the CAR construct into T cells can be accomplished by transducing (or otherwise delivering) a T cell composition with a recombinant DNA or RNA construct, such as for example, a vector. A vector may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

Selection of promoter and other regulatory sequences for protein expression are well known to those of skill in the art. Cell specific promoters for expression in T-cells include, but are not limited to, human CD2, distal Lck, and proximal Lck. In other embodiments, non-tissue specific promoters such as non-tissue specific promoters including viral promoters such as cytomegalovirus (CMV) promoter, β-actin promoter phosphoglycerate kinase (PGK) promoter, ubiquitin promoter, and EF-1α promoter can be used. This list is not meant to be limiting. An expression construction preferably also includes sequences to allow for the replication of the expression construct. Transcription of the DNA encoding the polypeptides of the present invention by higher eukaryotes may be increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers. Preferably, a retroviral vector (either gamma-retroviral or lentiviral) is employed for the introduction of the CAR nucleic acid construct into the cell. For example, a polynucleotide encoding a co-stimulatory ligand protein (e.g., tumor necrosis factor (TNF) ligand, such as 4-1BBL, OX40L, CD70, LIGHT, and CD30L, or an Ig superfamily ligand, such as CD80 and CD86), or a receptor that binds an antigen, or a variant, or a fragment thereof, can be cloned into a retroviral vector and expression can be driven from its endogenous promoter, from the retroviral long terminal repeat, or from a promoter specific for a target cell type of interest. Non-viral vectors may be used as well.

3. Inhibition of T Cell Proliferation in Recipients

The CAR-T cells of the present invention are expanded and activated in vitro to reach therapeutically sufficient numbers prior to administration to a subject. The cells may be expanded either non-specifically with mitogenic αCD3 and αCD28 antibodies, or through the use of genetically modified antigen-presenting cell lines or particles which display the antigen targeted by the CAR binding domain (and in some cases additional costimulatory molecules). Other methods to selectively propagate T cells to constitutively express CAR include co-expression with transgenes for selection under cytocidal concentrations of drug and/or sorting, such as using magnetic beads that recognize introduced proteins co-expressed with CAR. Antigen-specific expansion is preferred, as CAR-mediated T-cell activation is thought to depend on and to increase with the binding affinity to cognate antigen. In the event that the CAR-T cells of the present invention are non-specifically expanded without activation prior to treatment with a nucleic acid targeting agent, they may be activated in vitro prior to administration to a subject, again using cell lines or particles which display the antigen targeted by the CAR binding domain.

Prior to administration, and following expansion, the antigen-specific CAR-T cells are treated with a nucleic acid targeting agent, such as a cross-linking agent, a psoralen, a nitrogen mustard, cis-platin, a bulky adduct, ultraviolet light, gamma irradiation, any combination thereof, and the like. Typically, the lesion produced by one molecule of cross-linking agent involves cross-linking of both strands of the double helix, and most preferably the creation of inter-strand crosslinks in the DNA helix. Treatment of cells with a nucleic acid targeting agent, such as a light sensitive nucleic acid cross-linking agent (e.g., a psoralen followed by exposure to ultraviolet light) is described in U.S. Patent Publications 2004/0228877 and 2004/0197343 and in WO1999/003976. The use of such agents results in a proliferation incompetent CAR-T-derived effector cell population that maintains immunological activity, including the ability of the effector cell population to promote destruction of a diseased cell.

In a preferred embodiment, the nucleic acid targeting agent is present in an amount effective to form from about $10^2$ to about $10^4$ adducts per $10^8$ base pairs of genomic DNA of the leukocytes. Preferably, the method results in proliferation being inhibited in at least 90% of the CAR-T-derived effector cells. Suitable nucleic acid targeting agents comprise an alkylator selected from the group consisting of mustards, mustard intermediates and mustard equivalents; a nucleic acid targeting group selected from the group consisting of intercalators, minor groove binders, major groove binders, electrostatic binders, and sequence-specific binders; frangible anchor linker effector (FRALE) compounds (see e.g., U.S. Pat. Nos. 6,093,725 and 6,514,987) such as β-alanine; N-(acridin-9-yl), 2-[bis(2-chloroethyl)amino] ethyl ester; or a photoactivatable moiety selected from the group consisting of furocoumarins, actinomycins, anthracyclinones, anthramycins, benzodipyrones, fluorenes, fluorenones, monostral fats blue, norphillin A, organic dyes; phenanthridines, phenazathionium salts, phenazines, phenothiazines, phenylazides, quinolines and thiaxanthenones acridines and ellipticenes, or a combination thereof. Preferred are psoralen and psoralen-derived compounds activated by UVA irradiation (see e.g., U.S. Pat. Nos. 5,399,719 and 5,593,823). In a preferred embodiment, the psoralen is 4'-(4-amino-2-oxa)butyl-4,5',8-trimethylpsoralen, 4'aminomethyl 4, 5', 8-trimethylpsoralen (AMT), 5-methoxy psoralen, trioxalen 4, 5', 8-trimethylpsoralen, or 8-methoxy psoralen. This list is not meant to be limiting.

The number of covalent adducts that the compound forms in the CAR-T-derived effector cell nucleic acid can be modulated so that the compound inhibits proliferation but maintains immune functions effective to promote destruction of a diseased cell. With alkylator compounds, the effect can be modulated by adjusting the concentration of the compound and the length of time the leukocytes are contacted with the compound before removing unbound compound, as well as the addition of quenchers with different specificities The concentration required will depend on the characteristics of the particular compound, such as its solubility in aqueous solution and the DNA binding constant. The compound will typically be used at concentrations effective to generate about 1 to $10^4$ adducts of the covalent binding compound per $10^8$ base pairs of leukocyte genomic DNA, preferably about 5 to $10^3$ adducts, even more preferably, about $10^2$ to $10^3$ adducts. Ideally, the conditions for treating the leukocyte population will generate about $10^3$ adducts per $10^8$ base pairs of genomic DNA. The lowest concentration of compound effective to achieve the leukocyte compositions of the present invention is the preferred concentration. The number of adducts can be modulated by the presence of certain additives in the compositions being treated. For example, the use of human serum albumin (HSA) in the illumination mixture, to help stabilize T-cells during exposure to ultraviolet light, modifies the PCT exposure dose required for a given level of reaction. In the case of HSA, a quenching effect is obtained, such that a higher PCT exposure dose (e.g., higher compound concentration and/or higher light dose) is required for equivalent level of reaction. The use of additives, such as HSA, in the photochemical treatment reaction provides greater flexibility in defining conditions for achieving reproducible levels of reaction using higher compound concentrations and/or light doses. As another example glutathione or other thiol compounds can be used in addition to the alkylator compounds to modify their reactivity in different compartments of the cellular milieu, as well as the effective concentration of the compound reacting with nucleic acids to form adducts and crosslinks. It is expected that different thiol compounds will have different partitioning between the extra and intracellular domains. The choice of the thiol as well as the concentration can help modulate the number of adducts formed.

Where the compound used to treat the leukocytes is psoralen, the psoralen is can be present at a concentration in the range of $10^{-4}$ μM to 150 μM, more preferably $10^{-3}$ μM to 15 μM, still more preferably $10^{-3}$ μM to 1.5 μM; and the sample of leukocytes is exposed to ultraviolet light having a wavelength in the range of 200 to 450 nm, preferably between 320 and 400 nm. Preferably, the ultraviolet light is provided at a dosage of between $10^{-3}$ to 100 J/cm$^2$, more preferably, 0.1 to 10 J/cm$^2$. The sample of leukocytes will be exposed to the ultraviolet light for a period of 1 second to 60 minutes, preferably 6 seconds to 10 minutes. The sample of leukocytes will preferably be provided at a cell density of 10 to $10^9$ cells per mL, more preferably between $10^2$ and $10^8$ cells pre mL, most preferably at $2\times10^6$ cells per mL. The sample will preferably contain, in addition to 15 nM psoralen, approximately $2\times10^6$ cells/mL in 200 mL of solution also containing approximately 1% human serum albumin (HSA), 133 (g/ml) sodium caprylate, 197 (g/ml) sodium acetyltryptophanate, and 0.9% NaCl. The number of compound-DNA adducts resulting from treatment can be measured by methods known to those of skill in the art, for example, by using radiolabeled DNA binding compound as described in the Examples below, or by PCR analysis of long (e.g., 15-20 kilobase) amplicons (measuring the degree of inactivation of the amplicons) with statistical analysis of the results, as described by Yakes et al. (1997) *Proc. Natl. Acad. Sci. USA* 94:514-519.

The effect of treatment with the compound on the viability and function of the leukocyte population can be monitored by in vitro as well as in vivo assays to determine the optimum treatment conditions that minimize proliferation of the CAR-T-derived effector cells and cytokine release syndrome activity while maintaining cytotoxic function. While some cytokine production by the CAR-T-derived effector cells may be inhibited, preferably cytokine production is maintained at least 70%, more preferably at 80%, even more preferably greater than 90%, and most preferably at least greater than 95%, of the level before treatment with the aforementioned compound. The presence of antigenic markers, CD2, CD28, CTLA4, CD40 ligand (gp39), CD18, CD25, CD69 (lymphocyte activation marker) and CD16/CD56, which are known to be involved in interactions associated with T-cell and NK cell activation and immune function, can be determined as a function of concentration of the nucleic acid targeting agent. The effectiveness of a leukocyte population to promote destruction of a diseased cell or pathogen can be measured by various assays, such as by MLR or by $^{51}$Cr release assay as described below in the Examples. Cytolytic effectiveness is demonstrated, e.g., by the ability to mediate killing of a leukemic cell in a $^{51}$Cr release assay.

For the purposes of this invention, a CAR-T-derived effector cell population is considered effective to promote destruction of a diseased cell if, in an appropriate assay (e.g., the $^{51}$Cr release assay), the population exhibits cytolytic activity at a level of at least about 20% above that of the negative control population. In certain embodiments, the CAR-T-derived effector cell population may exhibit cytolytic activity (e.g., in an appropriate assay) at a level of at least about 50%, at least about 60%, at least about 70%, at least about 80%, at least about 90%, at least about 95% or more above that of the negative control population. The diseased cell can be from any type of cancer, of any tissue or cell type origin. Suitable target cells include but are not limited to cells of the following malignancies: Leukemia including Chronic Myelogenous Leukemia (CML), Chronic Lymphocytic leukemia (CLL), Acute Myelogenous Leukemia (AML), and Acute Lymphoblastic Leukemia (ALL); Multiple myeloma (MM); Non-Hodgkin lymphoma and Hodgkin's disease (lymphoma); solid tumors, including breast, lung, ovarian and testicular cancers, prostate cancer, colon cancer, melanoma, renal carcinoma cell, neuroblastoma, and head and neck tumors.

3. Target Cancer Antigens

The CARs and CAR-T-derived effector cell populations of the present invention preferably target one or more cancer antigens. Examples of target antigens that may find use in the invention are listed in the following table. The target antigen may also be a fragment or fusion polypeptide comprising an immunologically active portion of the antigens listed in the table. This list is not meant to be limiting.

TABLE 1

Antigens.

| Antigen | Reference |
|---|---|
| | Tumor antigens |
| CD19 | GenBank Acc. No. NM_001178098; NP_001171569; UniProt P15391 (The Lancet, Early Online Publication, 13 Oct. 2014 doi: 10.1016/S0140-6736(14)601403-3). |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |

TABLE 1-continued

Antigens.

| Antigen | Reference |
|---|---|
| Tumor antigens | |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; |

TABLE 1-continued

Antigens.

| Antigen | Reference |
|---|---|
| *Tumor antigens* | |
| e.g., mutations G12C; G12D; G12R; G12S; G12V; G13D; A59T; Q61H. K-RAS; H-RAS; N-RAS. | NM_033360; NM_176795; NM_005343. |
| BRAF (an isoform of RAF). | Tannapfel, et al. (2005) Am. J. Clin. Pathol. 123: 256-260l; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, eg., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |

TABLE 1-continued

Antigens.

| Antigen | Reference |
|---|---|
| | Tumor antigens |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published patent application No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See. e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |

4. Therapeutic Compositions

The cell compositions described herein can be administered to a host, either alone or in combination with a pharmaceutically acceptable excipient, in an amount sufficient to induce an appropriate anti-tumor response. The response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

The invention provides a method of providing an anti-tumor immunity in a mammal by administering to a mammal an effective amount of a cell genetically modified to express a CAR. An "effective amount" as used herein means an amount which provides a therapeutic or prophylactic benefit. Effective amounts of CAR T cells can be determined by a physician with consideration of individual differences in age, weight, tumor size, extent of infection or metastasis, and condition of the patient (subject). It can generally be stated that a pharmaceutical composition comprising the CAR T cells described herein may be administered at a dosage of $10^4$ to $10^{11}$ cells/kg body weight, preferably $10^7$ to $10^{10}$ cells/kg body weight, including all integer values within those ranges. T cell compositions may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

An effective amount of the cell compositions described herein may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

A "pharmaceutically acceptable excipient" or "diagnostically acceptable excipient" includes but is not limited to, sterile distilled water, saline, phosphate buffered solutions, amino acid based buffers, or bicarbonate buffered solutions. An excipient selected and the amount of excipient used will depend upon the mode of administration. Administration comprises an injection, infusion, or a combination thereof.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The cell compositions of the present invention can be administered in a dose, or dosages, where each dose comprises at least 100 cells/kg body weight or more; in certain embodiments 1000 cells/kg body weight or more; normally at least 10,000 cells; more normally at least 100,000 cells; most normally at least 1 million cells; often at least 10 million cells; more often at least 100 million cells; typically at least 1 billion cells; usually at least 10 billion cells; conventionally at least 100 billion cells; and sometimes at least 1 trillion cells/kg body weight.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Co-administration need to refer to administration at the same time in an individual, but rather may include administrations that are spaced by hours or even days, weeks, or longer, as long as the administration of multiple therapeutic agents is the result of a single treatment plan. By way of example, the CAR-T effector cells of the present invention may be co-administered with CAR-T cells having the same chimeric receptor, but which are not attenuated for proliferation as described herein. The co-administration may comprise administering the CAR-T effector cells of the present invention before, after, or at the same time as the "traditional" CAR-T cells. In a treatment schedule as described in FIG. 2, the CAR-T effector cells of the present invention may be given as an initial dose in a multi-day protocol, with "traditional" CAR-T cells given on later administration days; or the "traditional" CAR-T cells given as an initial dose in a multi-day protocol, with the CAR-T effector cells of the present invention given on later administration days. Alternatively, "traditional" CAR-T cells and the CAR-T effector cells of the present invention may be administered on alternate days in a multi-day protocol. In still another alternative, a mixture of "traditional" CAR-T cells and the CAR-T effector cells of the present invention may be administered to reduce the number of proliferation-competent cells in a single administration while maintaining an effective T cell dose. This is not meant to be a limiting list of possible administration protocols.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

Formulations of therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

EXAMPLES

The following examples serve to illustrate the present invention. These examples are in no way intended to limit the scope of the invention.

Example 1. Condition Mice with OVA Expressing Tumor Line (N=6-8 Mice Per Arm)

Specific pathogen-free, C57BL/6 (CD45.2, Thy-1.2), CD45.1, and Thy-1.1 congenic mice and OT-1 mice on a C57BL/6 (H-2b) background are obtained from commercial sources. The OT-1 mice express a transgenic TCR Va2 and Vb5 specific for the SIINFEKL peptide of OVA in the context of MHC class I, H2-Kb. Homozygous perforin2/2, TNF2/2 (OT-1.TNF), and IFN-g2/2 (OT-1.IFN-g) deficient C57BL/6 mice are generated by backcrossing OT-1 mice onto specified syngeneic deficient mice (H-2b) and the OT-1, cytokine-deficient, mice are selected from the F2 generation and obtained from commercial sources.

The OVA-transfected B16 tumor cell line (B16-OVA) is obtained from commercial sources and maintained in RPMI 1640, supplemented with 10% heat-inactivated FBS, 2 mmol/l L-glutamine, 100 mg/ml kanamycin, 50 mmol/l 2-ME, 0.024 mmol/l sodium bicarbonate, and 600 mg/ml G418 (Invitrogen. Carlsbad, Calif.).

Example 2. Isolate Compatible CD8 T-Cells with OVA Specificity/Expand when Necessary Spleens and lymph nodes are collected from OT-1 mice (7-8 weeks of age) and single-cell suspensions prepared by mechanical disruption. Cells are washed and resuspended in RPMI 1640 medium supplemented with 10% FBS, 1 mmol/l MEM sodium pyruvate, 0.1 mmol/l MEM nonessential amino acids, 2 mM L-glutamine, 100 IU penicillin, 100 mg/ml streptomycin (Invitrogen), 45 µM 2-ME (Sigma-Aldrich, St. Louis, Mo.). Live cells are obtained by density gradient centrifugation with Lympholyte M (Cedarlane Laboratories, Hornby, Ontario, Canada). Fc receptor binding is blocked with 2 mg/ml 2.4G2, and cells stained with anti-CD44 microbeads and CD44$^{hi}$ cells are depleted. The remaining CD$^{8+}$ CD44$^{lo}$ T cells are isolated by negative selection using a CD8+ T cell kit (Miltenyi Biotech, Auburn, Calif.) according to the manufacturer's protocol.

To obtain effector cells to OVA peptide, single cell suspensions from spleen and lymph nodes of designated OT-1 mice are washed twice in HBSS and resuspended in RPMI 1640/10% FCS. CD8-enriched T cells are obtained by passing lymphoid cell suspensions through nylon wool columns and treating with anti-CD4 (RL172.4), anti-heat-stable Ag (J11D), and anti-MHC class II (D3.137, M5114, CA4) mAbs and complement.

Small resting CD8 T cells are harvested from Percoll gradients (Sigma-Aldrich) and resuspended to appropriate cell concentrations in culture medium. Naive CD8 cells are typically 90% pure as demonstrated by immunofluorescent Ab staining.

APCs are enriched from spleens of normal C57BL/B6 mice by anti-Thy1.2 (H013.14 and F7D5), anti-CD4 (RL172.4), and anti-CD8 (3.155) mAbs, and complement. T cell-depleted APCs are pulsed with OVA peptide (10 µM) for 30 min at 37° C. and treated with mitomycin C (50 µg/ml; Sigma-Aldrich) for an additional 30 min at 37° C.

For Tc1 effector cell generation, naive CD8 T cells from OT-1 transgenic mice ($2\times10^5$ cells/ml) are stimulated with mitomycin C-treated, OVA peptide-pulsed APCs ($6\times10^5$ cells/ml) in the presence of IL-2 (20 U/ml, X63.IL-2 supernatants). IL-12 (2 ng/ml), and anti-IL-4 mAb (200 U/ml; X63.Ag.IL-4 supernatants). IL-2 supernatants), IL-12 (2 ng/ml), and anti-IL-4 mAb (10 mg/ml, 11B11). After 2 d of incubation, an equal volume of complete media containing IL-2 (20 U/ml) is added to the Tc1 cultures. Effector CD8 T cells subsets are harvested at day 4. The resulting Tc1 effector populations are restimulated in vitro and extensively analyzed to confirm that they express the properties established for Tc1 effectors.

T cells are washed, and expanded by addition of anti-CD3/CD28-coated paramagnetic beads for activation of T cells. On the final day of culture, the beads are removed by passage over a magnetic field and the cells are harvested.

Example 3. Treatment of Activated Cells with Amotosalen

The cell suspensions in RPMI aliquots (5 mL in 6 well plates, or equivalent vesicle), are dosed with 33 µL of stock solutions of amotosalen (15 mM, 1.5 mM, 150 µM, 15 µM, 1.5 µM) to final concentrations of amotosalen in the photo-illumination container of 100 µM, 10 µM, 100 nM and 1 nM, respectively. The solutions are illuminated with UVA light to a final dose equivalent of 3 J/cm$^2$ in a UVA illumination device. The illumination device is a microprocessor-controlled system that consists of two banks of UVA lights (me F15T12 BLB lamps, Spectronics Corp., New York, N.Y.) that deliver UVA light to the top and bottom of the plastic containers. Photodiodes continually monitor the output from the lamps. The microprocessor integrates the photodiode signals and adjusts the exposure time so that the previously programmed dose is delivered to within 0.1 J per cm$^2$. An internal cooling fan keeps the container with cells near the ambient temperature (22-24° C.) during illumination.

Amotosalen adduct frequency is determined by using $^{14}$C labeled amotosalen psoralen for photochemical inactivation. After photochemical treatment using the radioactively labeled amotosalen, genomic DNA is isolated form the T-Cells. The adduct frequency (defined as the base-pair interval between psoralen adducts) is determined by dividing the calculated DNA genomes by the S-59 psoralen molecules, determined from the DNA concentration, the radioactivity of each sample, and specific activity of $^{14}$C S-59 psoralen.

Alternatively, the effect of the illumination is correlated empirically with the effect that the CD8 cells will have in adoptive immunotherapy model as described below. Increasing concentrations of amotosalen will increase the modification of the nucleic acids, affecting firstly the ability to proliferate and then the ability to transcribe to RNA and to translate RNA to proteins and perform more complicated multi-molecular functions such as antigen presentation, or signal transduction. Additionally, the numbers of cells that will be necessary to cause the right effect will also depend on the level of modification used.

Example 4. Treatment of Preconditioned Mice with the Different Regiments

Adoptive T Cell Immunotherapy Model

Female CD45.2 or CD45.1 C57BL/6 mice receive a subcutaneous injection containing $2\times10^5$ B16-OVA melanoma cells resuspended in PBS. At day 7 or 12 after tumor injection, mice that have developed a palpable tumor receive an i.v. injection that contains varying doses of Tc1 in vitro generated effector cells. Control groups of mice are injected with PBS. The mice can be monitored for tumor size reduction. In alternate arrangements, the tumor cells are injected i.v. and the tumor will grow as lung tumor nodules, as a model for metastatic disease. Additionally, mouse may be implanted with tumor cells at several distinct locations. The mice are monitored for survival.

Evaluation of Endpoints:
Reduce Size of Existing Tumor

A week post inoculation with the B16-OVA melanoma cells, the animals are treated with different T-cell preparations. After treatment with the specific regiment of CD8T-

Cells, tumor size is measured three times a week using an engineering caliper. Tumor volume can be calculated by using the following formula:

Tumor volume(mm³)=(length)×(width)×0.4

Increase Survival

The survival of mice that have received an inoculum of B16-OVA melanoma cells i.v. is monitored over a period of 6 months. The results are plotted as a function of regiment used.

Prevent Tumor Establishment

C57BL/6-, IFN-g2, and TNF-deficient mice are injected with $2 \times 10^5$ B16-OVA cells. At day 7, mice are treated with different regiments of CD8 T-Cells. The percentage of tumor volume reduction is calculated at day 6 and plotted against control size numbers.

Example 5. Manufacture of CAR-T Cell-Derived Effector Cells

FIG. 1 depicts a manufacturing protocol for CAR-T cell-derived effector cells (B) as compared to a traditional Car-T cell protocol. As shown, peripheral blood mononuclear cells (PBMCs) are collected by leukapheresis, T cells are enriched by mononuclear cell elutriation, washed, and expanded by addition of anti-CD3/CD28-coated paramagnetic beads for activation of T cells. A lentiviral vector containing a CD19-BB-ζ (anti-CD19 attached to CD3ζ and 4-1BB signaling domains) transgene (Porter et al., 2011, NEJM 365:725-733) is added at the time of cell activation and is washed out on day 3 after culture initiation. Cells are expanded on a rocking platform device (WAVE Bioreactor System) for 8 to 12 days. On the final day of culture, the beads are removed by passage over a magnetic field and the transduced cells, designated CTL019 cells, are harvested. The cells are next treated with amotosalen/UVA at a concentration and dose optimized for anticancer cell properties while attenuated for proliferation (e.g., inhibited proliferation, unable to reproduce). After the conclusion of amotosalen/UVA treatment, the proliferation inhibited (iCAR) cells are cryopreserved in infusible medium. Final product release criteria includes the following: cell viability ≥70%, CD3+ cells ≥80%, residual paramagnetic anti-CD3/CD28-coated paramagnetic beads ≤100 per $3 \times 10^6$ cells, Endotoxin ≤3.5 EU/mL, Mycoplasma negative, bacterial and fungal cultures negative, residual bovine serum albumin ≤1 μg/mL, VSV-G DNA as a surrogate marker for replication competent lentivirus ≤50 copies per μg DNA, transduction efficiency by flow cytometry ≥2%, transduction efficiency by vector DNA sequence 0.02 to 4 copies per cell.

Example 6. Administration of CAR-T Cell-Derived Effector Cells

Pre-clinical studies have showed that large tumors could be ablated, and that the infusion of $2.2 \times 10^7$ CART cells could eradicate tumors comprised of $1 \times 10^9$ cells, for an in vivo E:T ratio of 1:42 in humanized mice (Carpenito et al., 2009, Proc Natl Acad Sci USA 106:3360-3365. Autologous T cells are engineered to express an extracellular single chain antibody (scFv) with specificity for CD19. In addition to CD19 scFv, the cells are transduced to express an intracellular signaling molecule comprised of either the TCRζ chain or a tandem signaling domain comprised of 4-1BB and TCRζ signaling modules. The scFv is derived from a mouse monoclonal antibody, and thus contains mouse sequences, and the signaling domains are entirely of the native human sequences. The CAR T cells are manufactured by isolating the T cells by apheresis, and using lentiviral vector technology (Dropulic et al., 2006, Human Gene Therapy, 17: 577-88; Naldini et al., 1996, Science, 272: 263-7; Dull et al., 1998, J Virol, 72: 8463-71) to introduce the scFv:TCRζ:4-1BB into CD4 and CD8 T cells, washed, expanded by addition of anti-CD3/CD28-coated paramagnetic beads for positive selection and activation of T cells, and treated with amotosalen/UVA as described above.

At the end of treatment, the transduced, amotosalen/UVA treated cells are cryopreserved in infusible cryomedia. After logging the cells in the investigational pharmacy, frozen cells are transported in dry ice to the subject's bedside. The cells are thawed at the bedside one bag at a time using a water bath maintained at 36° C. to 38° C. The bag is gently massaged until the cells have just thawed. There should be no frozen clumps left in the container. If the proliferation-incompetent CART-19 cell product appears to have a damaged or leaking bag, or otherwise appears to be compromised, it should not be infused.

The day of the first infusions, patients have a CBC with differential, and assessment of CD3, CD4 and CD8 counts since chemotherapy is given in part to induce lymphopenia. Without wishing to be bound by any particular theory, it is believed that an initial i.v. dose of $10^9$ to $10^{11}$ CART-19 cells is optimal for this protocol. The first dose is administered using a split dose on days 0 (10%), 1 (30%) and 2 (60%). Subjects receive infusion in an isolated room. Cells are given at an infusion rate as quickly as tolerated so that the duration of the infusion is approximately 10-15 minutes. The transduced T cells are administered by rapid intravenous infusion at a flow rate of approximately 10 mL to 20 mL per minute through an 18-gauge latex free Y-type blood set with a 3-way stopcock. Subjects' vital signs are assessed and pulse oximetry is done prior to dosing, at the end of the infusion and every 15 minutes thereafter for 1 hour and until these are stable and satisfactory. A blood sample for determination of baseline CART-19 level is obtained before infusion and 20 minutes post infusion. Patients experiencing toxicities from their preceding cytoreductive chemotherapy have their infusion schedule delayed until these toxicities have resolved. The specific toxicities warranting delay of T cell infusions include: 1) Pulmonary: Requirement for supplemental oxygen to keep saturation greater than 95% or presence of radiographic abnormalities on chest x-ray that are progressive; 2) Cardiac: New cardiac arrhythmia not controlled with medical management. 3) Hypotension requiring pressor support. 4) Active Infection: Positive blood cultures for bacteria, fungus, or virus within 48-hours of T cell infusion. A serum sample for potassium and uric acid is collected before the first infusion as well as two hours after each subsequent infusion. Endpoint assays are conducted at designated intervals, such as on study week 4, in order to determine the efficacy of the treatment.

Example 7. Co-Administration with Proliferation-Competent CAR-T Cells

In protocols in which traditional CAR-T cells are co-administered with the CAR-T cell-derived effector cells of the present invention, The amount of CAR-T cells necessary per patient is determined in humanized mice as described in Rohena, K. M. Haines, D. F. Heitjan, S. M. Albelda, R. G. Carroll, J. L. Riley, I. Pastan, C. H. June, Proc Natl Acad Sci USA 106, 3360 (2009). Alternatively, patients are infused with $1-10 \times 10^7$ proliferation-competent T cells/kg or higher ($5-50 \times 10^8$ T cells for patients ≥50 kg) over 1-3 days. The CAR-T cell-derived effector cells of the present invention are then administered as a boost of the original unmodified CAR-T cell prep/infusion.

Example 8. References

Lee D W et al. Blood 2014, 124 188-195
Brockstedt D G et al. MEDICINE VOL 11 NUM 8 Aug. 2005, 853
Maus M V et al. Blood. 2014 123(17) 2625-2635
Garcia-Hernandez et al. J Immunol, 2010, 184: 4215-4227
Dobrzanski et al. J Immunol, 2004 172 1380-1390
Hei D et al., 39, 1999, TRANSFUSION 239

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A CAR-T cell-derived effector cell population comprising:
a population of activated T cells expressing a chimeric antigen receptor (CAR), the CAR comprising an extracellular domain which specifically binds a predetermined antigen, a transmembrane domain, and a cytoplasmic co-stimulatory signaling domain, wherein the nucleic acid of the activated T cells have been modified by reaction with a nucleic acid targeting compound that reacts directly with the nucleic acid so that the activated T cells are attenuated for proliferation, wherein the activated T cells are present in the population in a therapeutically effective amount for treatment of a malignancy that expresses the predetermined antigen.

2. The CAR-T cell-derived effector cell population of claim 1, wherein the nucleic acid targeting compound is a nucleic acid alkylator.

3. The CAR-T cell-derived effector cell population of claim 2, wherein the nucleic acid alkylator is a FRALE such as β-alanine, N-(acridin-9-yl), 2-[bis(2-chloroethyl)amino] ethyl ester.

4. The CAR-T cell-derived effector cell population of claim 1, wherein the nucleic acid targeting compound is activated by illumination.

5. The CAR-T cell-derived effector cell population of claim 4, wherein the nucleic acid targeting compound is a psoralen compound activated by UVA illumination.

6. The CAR-T cell-derived effector cell population of claim 5, wherein the activated T cells comprise psoralen-induced interstrand crosslinks introduced between the strands of the genomic DNA double helix.

7. The CAR-T cell-derived effector cell population of claim 6, wherein said interstrand crosslinks inhibit replication of the activated T cells.

8. The CAR-T cell-derived effector cell population of claim 5, wherein the psoralen is 4'-(4-amino-2-oxa)butyl-4, 5',8-trimethylpsoralen, 4'aminomethyl 4, 5', 8trimethylpsoralen (AMT), 5-methoxy psoralen, trioxalen 4, 5' 8-trimethylpsoralen, or 8-methoxy psoralen.

9. The CAR-T cell-derived effector cell population of claim 1, wherein at least a portion of the activated T cells produce one or more cytokines.

10. The CAR-T cell-derived effector cell population of claim 9, wherein at least a portion of the activated T cells produce one or more cytokines selected from the group consisting of IL-1 IL-2, IL-4, IFN-γ, IL-10 and GM-CSF.

11. The CAR-T cell-derived effector cell population of claim 1, wherein at least a portion of the activated T cells express one or more surface markers selected from the group consisting of CD2, CD28, CTLA4, CD40 ligand (gp39), CD18, CD25, CD69, CD16/CD56, MHC Class I, MHC Class II, CD8, CD4, CD3/TcR, CD54, LFA-1 and VLA-4.

12. The CAR-T cell-derived effector cell population of claim 1, wherein greater than 90% of the activated T cells in the population are non-proliferating.

13. The CAR-T cell-derived effector cell population of claim 1, wherein the predetermined antigen is a cancer antigen.

14. The CAR-T cell-derived effector cell population of claim 13, wherein the predetermined antigen is selected from the antigens listed in Table 1.

15. The CAR-T cell-derived effector cell population of claim 13, wherein the cancer is selected from the group consisting of lung cancer, melanoma, breast cancer, prostate cancer, colon cancer, renal cell carcinoma, ovarian cancer, neuroblastoma, rhabdomyosarcoma, leukemia and lymphoma.

16. The CAR-T cell-derived effector cell population of claim 15, wherein the cancer is Hodgkin's lymphoma or childhood acute lymphoblastic leukemia.

17. A method of inducing a T-cell response to at least one predetermined antigen in a subject, comprising:
administering to the subject a CAR-T cell-derived effector cell population of claim 1 in an amount sufficient to induce an anti-tumor response to a cancer in the subject, wherein the cancer expresses the predetermined antigen.

18. A method according to claim 17, wherein the cancer is selected from the group consisting of lung cancer, melanoma, breast cancer, prostate cancer, colon cancer, renal cell carcinoma, ovarian cancer, neuroblastoma, rhabdomyosarcoma, leukemia and lymphoma.

19. A method according to claim 18, wherein the cancer is Hodgkin's lymphoma or childhood acute lymphoblastic leukemia.

20. A method according to claim 17, wherein the predetermined antigen is selected from the antigens listed in Table 1.

21. A method of preparing a CAR-T cell-derived effector cell population comprising a population of activated T cells expressing a chimeric antigen receptor (CAR), the CAR comprising an extracellular domain which specifically binds a predetermined antigen, comprising:
    contacting in vitro one or more T cells that have been modified to express the CAR with a stimulus that induces expansion of the T cells to provide an expanded T cell population;
    modifying the nucleic acid of the T cells in the expanded T cell population by reaction with a nucleic acid targeting compound that reacts directly with the nucleic acid so that the T cells in the expanded T cell population are attenuated for proliferation; and
    prior to or following the modifying step, activating in vitro the T cells to produce an effector T cell population.

22. A method according to claim 21, wherein the method comprises contacting the one or more T cells with the predetermined antigen under conditions in which the T cells are both induced to expand and are activated by the same stimulus, and the T cells in the expanded T cell population are attenuated for proliferation following expansion and activation.

23. A method according to claim 21, wherein the stimulus that induces expansion of the T cells is a non-specific expansion stimulus, and wherein the expanded T cell population is subsequently activated by contacting the T cells in the expanded T cell population with the predetermined antigen under conditions in which the T cells are activated.

24. A method according to claim 23, wherein the T cells in the expanded T cell population are attenuated for proliferation following expansion and activation.

25. A method according to claim 21, wherein the nucleic acid targeting compound is a nucleic acid alkylator.

26. A method according to claim 25, wherein the nucleic acid alkylator is a FRALE such as β-alanine, N-(acridin-9-yl), 2-[bis(2-chloroethyl)amino] ethyl ester.

27. A method according to claim 21, wherein the nucleic acid targeting compound is activated by irradiation.

28. A method according to claim 27, wherein the nucleic acid targeting compound is a psoralen compound activated by UVA irradiation.

29. A method according to claim 28, wherein the activated T cells comprise psoralen-induced interstrand crosslinks introduced between the strands of the genomic DNA double helix.

30. A method according to claim 28, wherein said interstrand crosslinks inhibit replication of the activated T cells.

31. A method according to claim 28, wherein the psoralen is 4'-(4-amino-2-oxa)butyl-4,5',8-trimethylpsoralen, 4'aminomethyl 4, 5', 8trimethylpsoralen (AMT), 5-methoxy psoralen, trioxalen 4, 5' 8-trimethylpsoralen, or 8-methoxy psoralen.

32. A method according to claim 21, wherein at least a portion of the activated T cells produce one or more cytokines.

33. A method according to claim 32, wherein at least a portion of the activated T cells produce one or more cytokines selected from the group consisting of IL-1 IL-2, IL-4, IFN-γ, IL-10 and GM-CSF.

34. A method according to one of claims 21-33, wherein at least a portion of the activated T cells express one or more surface markers selected from the group consisting of CD2, CD28, CTLA4, CD40 ligand (gp39), CD18, CD25, CD69, CD16/CD56, MHC Class I, MHC Class II, CD8, CD4, CD3/TcR, CD54, LFA-1 and VLA-4.

35. A method according to claim 21, wherein greater than 90% of the activated T cells in the population are non-proliferating.

36. A method according to claim 21, wherein the predetermined antigen is a cancer antigen.

37. A method according to claim 36, wherein the predetermined antigen is selected from the antigens listed in Table 1.

38. A method according to claim 36, wherein the cancer is selected from the group consisting of lung cancer, melanoma, breast cancer, prostate cancer, colon cancer, renal cell carcinoma, ovarian cancer, neuroblastoma, rhabdomyosarcoma, leukemia and lymphoma.

39. A method according to claim 36, wherein the cancer is Hodgkin's lymphoma or childhood acute lymphoblastic leukemia.

* * * * *